United States Patent
Smith, III et al.

(10) Patent No.: US 7,514,563 B2
(45) Date of Patent: Apr. 7, 2009

(54) PROCESS FOR PRODUCING CYANO SUBSTITUTED ARENE BORANES AND COMPOUNDS

(75) Inventors: Milton R. Smith, III, East Lansing, MI (US); Robert E. Maleczka, DeWitt, MI (US); Ghayoor A. Chotana, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 8 days.

(21) Appl. No.: 11/449,280

(22) Filed: Jun. 8, 2006

(65) Prior Publication Data

US 2006/0281939 A1 Dec. 14, 2006

Related U.S. Application Data

(60) Provisional application No. 60/689,161, filed on Jun. 9, 2005.

(51) Int. Cl.
- C07D 207/30 (2006.01)
- C07D 211/78 (2006.01)
- C07D 323/02 (2006.01)
- C07C 255/51 (2006.01)
- C07F 5/02 (2006.01)

(52) U.S. Cl. .......................... 546/286; 546/287; 549/4; 549/5; 549/213; 558/419; 558/442; 568/2; 568/6

(58) Field of Classification Search ................ 548/402, 548/405, 413; 546/286, 287; 549/4, 5, 213; 558/419, 422; 568/2, 6
See application file for complete search history.

(56) References Cited

U.S. PATENT DOCUMENTS 6,969,716 B2 * 11/2005 Blackaby et al. ............ 514/242

* cited by examiner

*Primary Examiner*—James O Wilson
*Assistant Examiner*—Ebenezer Sackey
(74) *Attorney, Agent, or Firm*—Ian C. McLeod

(57) ABSTRACT

A process for producing cyano substituted arene boranes is described. The compounds are useful intermediates to pharmaceutical compounds using the cyano group as a reactant.

17 Claims, 10 Drawing Sheets

PROCESS FOR PRODUCING CYANO SUBSTITUTED ARENE BORANES AND COMPOUNDS

CROSS-REFERENCE TO RELATED APPLICATION

This application relies for priority on U.S. provisional application Ser. No. 60/689,161, filed Jun. 9, 2005.

STATEMENT REGARDING FEDERALLY SPONSORED RESEARCH OR DEVELOPMENT

This invention was supported in part by National Institutes of Health, National Institute of General Medical Sciences Grant No. R01 GM63188-01. The U.S. government has certain rights in this invention.

BACKGROUND OF THE INVENTION (1) Field of the Invention

The present invention relates to a process for producing a cyano ring-substituted arene or heteroarene borane which comprises reacting a ring-substituted cyano arene or heteroarene with an HB or B—B organic compound in the presence of a catalytically effective amount of an iridium complex with three or more substituents, excluding hydrogen, bonded to the iridium and an organic ligand, which is at least in part bonded to the iridium, to form the ring-substituted cyano substituted arene or heteroarene borane.

(2) Description of Related Art

Alkyl and arylboronic esters and acids are versatile alkyl and aryl transfer reagents in organic chemistry wherein the boron serves as a "mask" for a broad range of heteroatoms and functional groups. Some of the most remarkable and broadly used applications of organoboron chemistry are catalytic cross-coupling reactions of C—B and C—X (X=Cl, Br, or I) groups which yield new C—C bonds as shown below.

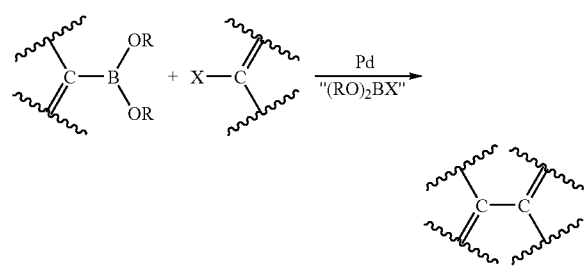

In the pharmaceutical industry, organoboron complexes are key building blocks for drug manufacturing, versatile reagents for high-throughput parallel synthesis in drug discovery, and exhibit some useful and unique biological activities.

Arylboronate esters and the corresponding acids are presently prepared by reacting Grignard reagents generated from halogenated aromatics and magnesium metal with alkyl borate reagents. A related method involves the reaction of alkyllithium reagents with aromatic halides or arenas to generate lithium reagents which are subsequently reacted with alkyl borates. Moreover, introduction of the Bpin group using other methods, such as Miyaura's cross-coupling reactions of alkoxydiboron reagents and aryl halides, are inconvenient because access to the 2-halogenated compounds is extremely limited (Ishiyama, T. et al., J. Org. Chem. 1995, 60, 7508-7510). Significant limitations of the current technologies include: (1) the reactions are run typically in ethereal solvents, (2) halogenated aromatics must be synthesized from hydrocarbon feedstocks, (3) for large-scale synthesis, unreacted chlorinated aromatic starting materials and biaryl byproducts can create significant environmental hazards and pose waste disposal problems, (4) in some instances attempted product isolation has resulted in explosions attributed to unreacted lithium and magnesium intermediates, (5) Grignard and organolithium reagents can be incompatible with a range of common functional groups including esters, amides, bromides, chlorides, iodides, alcohols, acids, and the like, and (6) cryogenic cooling is sometimes required to prevent side reactions.

Aromatic hydrocarbons are fundamental chemical building blocks, and their reactivity is a cornerstone of organic chemistry. Their utility derives largely from the regiochemical fidelity embodied in electrophilic aromatic substitutions (Taylor, R., Electrophilic Aromatic Substitution; John Wiley and Sons: New York, 1990). While steric effects can influence electrophilic aromatic substitution, electronic effects typically dominate. For electrophilic aromatic substitution (EAS) reactions, substituents on aromatic rings fall into two classes: ortho, para directors and meta directors. When directing groups are positioned to work in concert, regioselectivity can be complete as in the classic example of nitration at the 3-postion of 4-bromobenzonitrile (Scheme 1, electronically preferred product, FG=NO$_2$) (Schopff, M., Ber. 1890, 23, 3435-3440). For most disubstituted benzenes, EAS does not usually offer well-defined regiochemical outcomes. For example, two of the three possible arrangements of directing groups in 1,4-substituted benzenes give poor regioselectivity as shown in Scheme 1.

Scheme 1

Regiochemical trends in electrophilic aromatic substitution (EAS) for 1,4-substituted benzenes ortho/para directors

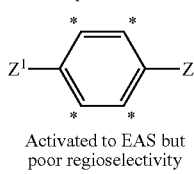

Activated to EAS but poor regioselectivity

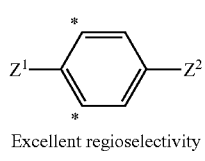

Excellent regioselectivity meta directors

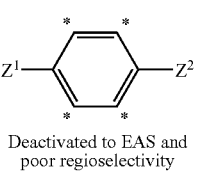

Deactivated to EAS and poor regioselectivity

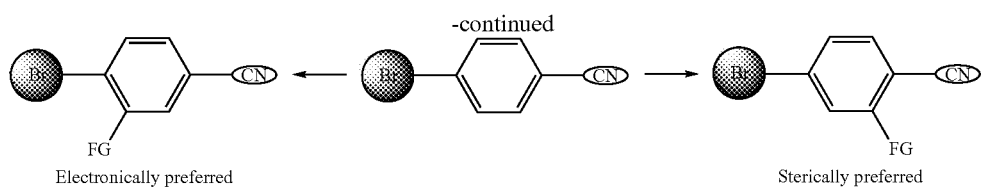

Electronically preferred

Sterically preferred

For the functionalization at positions meta to ortho, para directors and/or ortho to meta directors, alternate methods to electrophilic aromatic substitutions are required. In the case of certain meta directing substituents, directed ortho metalation (DoM) constitutes a powerful method for functionalization at the adjacent positions, provided that the substituent is a sufficiently strong directed metalation group (DMG) (Whisler, M. C., MacNeil, S.; Snieckus, V.; Beak, P., Angew. Chem. Int. Edit. 2004, 43, 2206-2225). For disubstituted benzenes, the regioselectivity of DoM depends on the positions of the substituents and their ranking in the DMG hierarchy. 1,3-Subsituted benzenes can often be derivatized selectively at the 2-position because DMG's can act in concert to direct metalation.

In contrast, DMG's can compete in 1,2- and 1,4-substituted benzenes. Therefore high regioselectivities are typically realized when there is a substantial difference in relative DMG powers. For example, while DoM protocols can be effective for functionalizing ortho to cyano groups in simple aromatic nitriles,(Kristensen, J.; Lysen, M., Vedso, P., Begtrup, M., Org. Lett. 2001, 3, 1435-1437; (b) Pletnev, A. A.; Tian, Q. O., Larock, R. C., J. Org. Chem. 2002, 67, 9276-9287) the presence of other groups can subvert the selectivity. Sometimes the regiochemical outcome is unexpected. For instance, competitive 2,5-dilithiation of 4-bromobenzonitrile occurs with LDA (Lulinski, S., Serwatowski, J., J. Org. Chem. 2003, 68, 9384-9388) and deprotonation at the 3-position has been reported with the hindered phosphazene base, $P_4$-t-Bu, (Imahori, T., Kondo, Y., J. Am. Chem. Soc. 2003, 125, 8082-8083) even though the DMG ranking of CN is greater than Br. In fact, there are no documented transformations of 4-bromobenzonitrile that are selective for the 2-position. Moreover, examples of functionalization at the 2-position in other 4-substituted benzonitriles are limited, and there are no general approaches toward this end (Wang, C et al., J. Org. Chem. 1998, 63, 9956-9959; Kim, B. H., et al. J. Chem. Soc.-Perkin Trans. 1 2001, 2035-2039; and Sonoda, M., S., Bull. Chem. Soc. Jpn. 1997, 70, 3117-3128). This is unfortunate because aryl nitrites have a rich chemistry, and are particularly useful entries into heterocyclic systems (Meyers, A. I., et al., The Chemistry of the Cyano Group. In the Chemistry of the Functional Groups; Patai, S. et al., Eds. Wiley & Sons: New York, 1970; Chapter 8; Fatiadi, A. J., In Supplement C: The Chemistry of the Triple-bonded Functional Groups; Patai, S., et al Eds. Wiley & Sons: New York, 1983; Chapter 26).

An alternate strategy for functionalizing benzonitriles that can potentially complement electrophilic aromatic substitutions and DoM's is to differentiate positions based on steric effects (Scheme 1). Since the first report by Ittel and coworkers in 1976, (Ittel, S. D. et al., J. Am. Chem. Soc. 1976, 98, 6073-6075) there have been several reports of transition metal mediated C—H activations where steric, not electronic, effects are the overriding factors in regioselection. More recently, significant progress has been made in coupling C—H activation with subsequent transformations of the nascent M-C bond to design new catalytic processes (Goldberg, K. I. et al., Activation and Functionalization of C—H Bonds. American Chemical Society: Washington, D.C. 2004). Since 1999, we,(Iverson, C. N., et al., J. Am. Chem. Soc. 1999, 121, 7696-7697; Cho, J.-Y et al., J. Am. Chem. Soc. 2000, 122, 12868-12869; Cho, J. Y., et al Science 2002, 295, 305-308; Maleczka, R. E., Jr. et al, J. Am. Chem. Soc. 2003, 125, 7792-7793; Chotana, G. A. et al., J. Am. Chem. Soc. 2005, 127, 10539-10544; Tse, M. K. et al., Org. Lett. 2001, 3, 2831-2833; Holmes, D. et al., Org. Lett. 2006, 8, 1407-1410; and Shi, F. et al., Org. Lett. 2006, 8, 1411-1414); and others, (Ishiyama, T. et al., J. Am. Chem. Soc. 2002, 124, 390-391; Ishiyama, T. et al., Angew. Chem. Int. Edit. 2002, 41, 3056-3058; Takagi, J et al., Tetrahedron Lett. 2002, 43, 5649-5651; Ishiyama, T. et al., Chem. Commun. 2003, 2924-2925; Ishiyama, T. et al., Adv. Synth. Catal. 2003, 345, 1103-1106; and Mertins, K. et al., J. Mol. Catal. A: Chem. 2004, 207, 21-25) have been particularly interested in utilizing Ir-catalyzed borylations of arenes to tap the unique regioselectivities available to sterically directed C—H activations.

In light of the above limitations of the current processes for producing cyano substituted arene boronate esters and acids, there remains a need for a synthetic route to synthesizing boronate esters and acids that does not have the limitations of the current processes.

Objects

It is an object of the present invention to provide a process for synthesizing cyano substituted arene or heteroarene boranes. A further object of the present invention is to provide a process for synthesizing ring-substituted cyano boranes by metal catalyzed activations of C—H bonds in arenes or heteroarenes and B—H or B—B bonds in boron reagents to produce novel B—C bonds. These and other objects of the present invention will become increasingly apparent with reference to the following drawings and preferred embodiments.

SUMMARY OF THE INVENTION

This application incorporates by reference in its entirety the disclosure in relation to the catalysts and organic ligands of U.S. Pat. No. 6,878,830.

The present invention relates to a process for producing a cyano substituted arene borane which comprises: reacting a ring-substituted cyano arene, wherein arene is 4, 5 or 6 carbon atoms and optionally is heterocyclic with an HB or B—B organic compound, in the presence of a catalytically effective amount of an iridium complex with three or more substituents, excluding hydrogen, bonded to the iridium with an organic ligand in the complex to form the cyano substituted ring-substituted arene borane.

The present invention also relates to a process for producing a di or tri ring-substituted cyano substituted arene borane which comprises: reacting a di or tri ring-substituted cyano arene, wherein arene is 4, 5 or 6 carbon atoms and optionally heterocyclic, with an HB or B—B organic compound in the presence of a catalytically effective amount of an iridium complex with three or more substituents, excluding hydrogen, bonded to the iridium and a dipyridyl organic ligand, in a molar ratio of complex to ligand between about 1 to 3 and 1 to 1, wherein the ligand is at least in part bonded to the iridium, to form the di or tri ring-substituted cyano substituted arene borane.

The present invention also relates to a cyano substituted arene borane ring compound comprising 4, 5 or 6 carbon atoms in the ring, which is optionally fused with aromatic rings and which is optionally heterocyclic, wherein there is at least one ring substituent other than hydrogen selected from the group consisting of halo other than fluoro, alkyl, alkoxy, thioalkyl, amino, alkyl acyl, alkyl aminoacyl, trifluoro methyl, substituted aryl, organosilane, organoborane, organostannane and phosphorous each typically containing 1 to 8 carbon atoms except for the halo group. Preferably the arene ring is a benzene ring.

The present invention also relates to a process for producing a ring-substituted arene borane which comprises: reacting a ring-substituted arene containing one to five substituents of which one or more is a cyano group, and wherein the arene is 4, 5 or 6 carbon atoms and optionally heterocyclic and including polycyclic rings with an HB or B—B organic compound, in the presence of a catalytically effective amount of an iridium complex with three or substituents, excluding hydrogen, bonded to the iridium, and a nitrogen substituent organic ligand, in a molar ratio of complex to ligand between about 1 to 3 and 1 to 1, wherein the ligand is at least in part bonded to the iridium, to form a ring-substituted arene borane containing two to six substituents at least one of which is cyano group. Preferably the borane moiety is ortho to a cyano group in the ring-substituted arene borane produced. Preferably the nitrogen organic ligand is selected from the group consisting of:

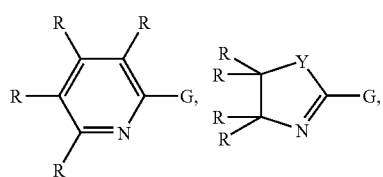

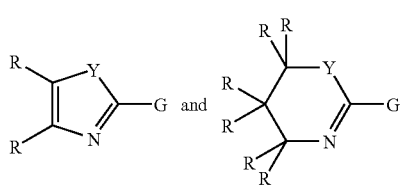

wherein R are each selected from the group consisting of hydrogen, linear alkyl containing 1 to 8 carbon atoms, branched alkyl containing 1 to 8 carbons, and a carbon in a cyclic structure, Y is a carbon, oxygen, nitrogen, or sulfur containing moiety, and G is a heteroatom containing group, multiple atom chain, or multiple atom ring. Preferably the nitrogen organic ligand is selected from the group consisting of:

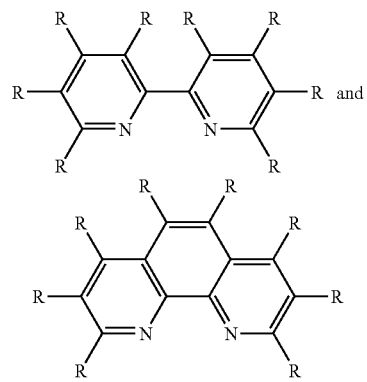

wherein R are each selected from the group consisting of hydrogen, linear alkyl containing 1 to 8 carbon atoms, branched alkyl containing 1 to 8 carbons, and a carbon in a cyclic structure. Preferably the nitrogen organic ligand is selected from the group consisting of:

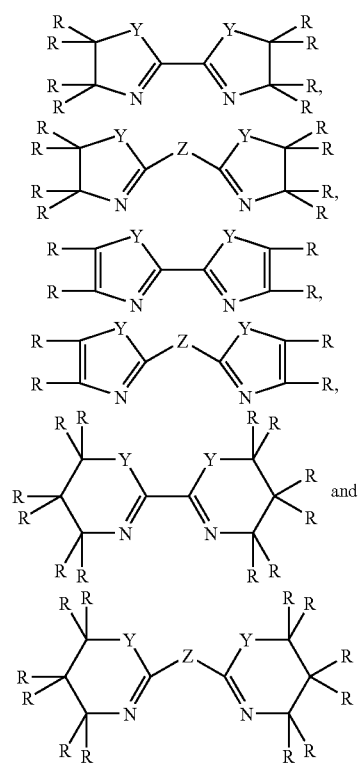

wherein R are each selected from the group consisting of hydrogen, linear alkyl containing 1 to 8 carbon atoms, branched alkyl containing 1 to 8 carbons, and a carbon in a cyclic structure, Y is a carbon, oxygen, nitrogen, or sulfur containing moiety, and Z is a carbon, oxygen, nitrogen, sulfur, or boron containing moiety or a multiple atom chain containing a carbon, oxygen, nitrogen, sulfur, or boron containing moiety.

Preferably the HB or B—B organic compound is HBPin or $B_2Pin_2$. Still further, the present invention relates to the process wherein the complex is an iridium complex of [Ir(OMe)

(COD)]$_2$, where COD is 1,5-cyclooctadiene complexed with 4,4'-di-t-butyl-2,2'-bipyridine (dtbpy).

Preferably a benzonitrite of the formula:

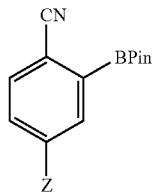

wherein BPin is

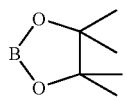

and Z is selected from the group consisting of —Cl, Br, —I, —CH$_3$, —OMe, —SMe —NMe$_2$, —CO$_2$Me, NHAc and CF$_3$ moieties.

Catalysts

The present invention provides a catalytic composition comprising an iridium complex with three or more substituents, excluding hydrogen, bonded to the iridium. In a further embodiment, the present invention provides a catalytic composition comprising an iridium complex with three or more substituents, excluding hydrogen, bonded to the iridium and an organic ligand selected from the group consisting of a phosphorus organic ligand, or a nitrogen organic ligand such as an organic amine, an imine, a nitrogen heterocycle, and an ether in a molar ratio between about 1 to 3 and 1 to 1, wherein the ligand is at least in part bonded to the iridium complex.

In an embodiment of the catalytic composition, the iridium complex is selected from the group consisting of (Cp*)Ir(H)$_2$ (Me$_3$P), (Cp*)Ir(H)(BPin)(Me$_3$P), (CP*)Ir(H)(C$_6$H$_5$)(Me$_3$P), (Ind)Ir(COD), (MesH)Ir(BPin)(B(OR)$_2$), ((R$_1$)$_3$P)$_3$Ir(B(OR$_2$)$_2$)$_3$, (R$_1$)$_2$P)$_2$Ir(BPin)$_3$, [((R$_1$)$_2$P)$_3$Ir((R$_2$O)$_2$B)$_3$]$_2$, ((R$_1$)$_3$P)$_4$Ir(BPin), ((R1)$_2$P)$_2$Ir(BPin)$_3$, (MesH)Ir(BPin)$_3$, IrCl(COD), [IrCl(COD)]$_2$, and [Ir(OMe)(COD)]$_2$. In the foregoing, CP* is 1,2,3,4,5-methylcyclopentadienyl, BPin is pinacolborane, Me is methyl, H is hydrogen, P is phosphorus, Ind is indenyl, COD is 1,5-cyclooctadiene, and MesH is mesitylene. Further R, R$_1$, and R$_2$ are each selected from the group consisting of hydrogen, linear or branched alkyl containing 1 to 8 carbons, aryl, and a carbon in a cyclic structure.

The catalytic composition also can include an iridium complex of the formula: (BY)$_n$—Ir-(ligand)$_m$ with three or more n and m substituents, excluding hydrogen, bonded to the iridium BY is a boron moiety and the ligand is selected from the group consisting of a phosphorus organic ligand, an organic amine, an imine, a nitrogen heterocycle, and an ether wherein the ligand is at least in part bonded to the iridium.

DETAILED DESCRIPTION OF THE DRAWINGS

DESCRIPTION OF PREFERRED EMBODIMENTS

Figure 1:
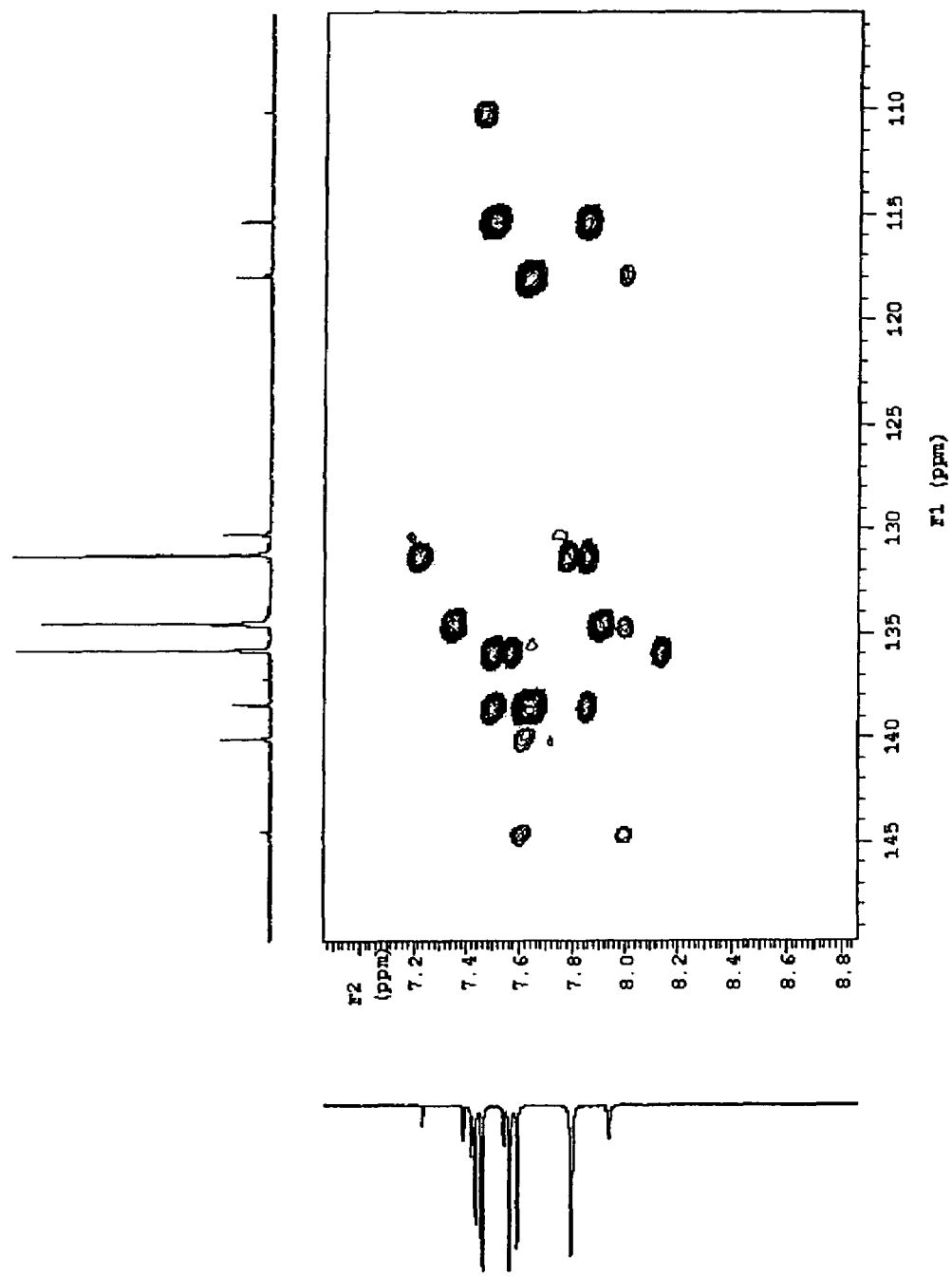
FIG. 1 is a gHMBC spectrum of the borylation products of 4-chlorobenzonitrile.

All patents, patent applications, provisional patent applications, government publications, government regulations, and literature references cited in this specification are hereby incorporated herein by reference in their entirety. In case of conflict, the present description, including definitions, will control.

Ir-catalyzed borylations of 4-substituted benzonitriles are described hereinafter. In contrast to electrophilic aromatic substitutions and directed ortho metalations, C—H activation/borylation enables functionalization at the 2-position, adjacent to the cyano group, when the 4-subsitutent is larger than cyano. When an excess of borane reagent is used, diborylation can be achieved with a single regioisomer being formed in certain cases. Extension of sterically directed borylation to cyano substituted, 5- and 6-membered ring heterocycles is also described.

Borylation ortho to nitrile groups should be possible for appropriate substrates since the cyano group is only slightly larger than fluoride. Initial attempts to borylate benzonitriles with pinacolborane (HBPin) using Ir phosphine systems at elevated temperatures gave complex mixtures due to competitive reduction of the nitrile. These catalysts can provide a lower temperature; however, other catalysts were available. More active Ir catalysts developed by Hartwig, Ishiyama, and Miyaura (Ishiyama, T., et al., J. Am. Chem. Soc. 2002, 124, 390-391) overcome this problem. These Ir dipyridyl catalysts operate at room temperature, and examples have been reported showing that the nitrile group is compatible with the borylation conditions. However, data are available for only three substrates, none of which addressed the regiochemical hypothesis. The following results show borylations ortho to cyano groups of benzonitriles.

Results

Borylations of 4-substituted benzonitriles were examined. As most substrates were poorly soluble in saturated hydrocarbons, borylations were typically carried out in tetrahydrofuran (THF) solvent using the catalyst constituted from a 1:2 ratio of [Ir(OMe)(COD)]$_2$ (COD=1,5-cyclooctadiene) and 4,4'-di-t-butyl-2,2'-bipyridine (dtbpy) as indicated in Scheme 2. The results for monoborylation reactions are given in Table 1. The reaction times roughly correspond to relative reactivities and yields are for isolated products with respect to the limiting reagent. Either HBPin or B$_2$Pin$_2$ can be used with shorter reaction times required for the latter reagent. Diborylation can be significant when the benzonitrile is the limiting reagent. For these substrates, a benzonitrile: borane reagent ratio of 4:1 was used to minimize diborylation.

Scheme 2

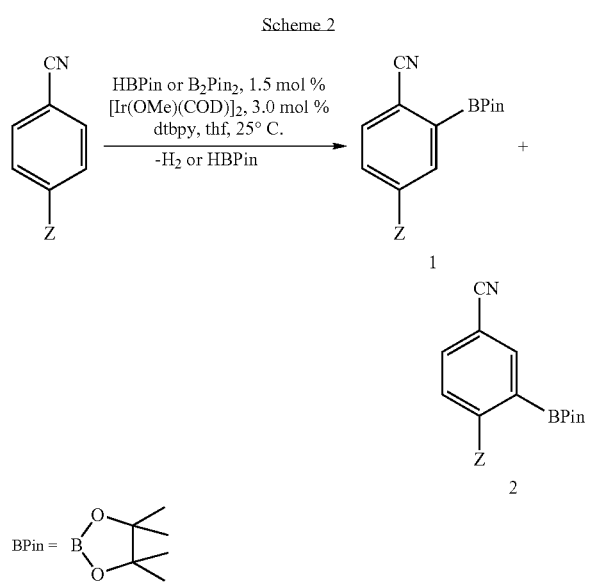

For 4-halobenzonitriles, the extent of borylation at the 3-position (isomer 2) diminishes in the order F>Cl>Br>I. This trend is consistent with the ordering of steric energies for substituents on a benzene ring F<CN<Cl<Br<I. However, the regioselectivities are also consistent with the thermodynamic ordering of ortho-C—H acidities F>CN>Cl from the literature (Stratakis, M. et al., J. Org. Chem. 1996, 61, 3145-3150; and Krizan, T. D. et al., J. Am. Chem. Soc. 1983, 105, 6155-6157). Thus, rationalization of the regiochemical outcome is shackled with the age-old dilemma of definitively separating steric and electronic effects. Nevertheless, a compelling case can be made for steric directing effects as outlined below.

TABLE 1

Regioselectivities for borylation of 4-benzonitriles.[a]

| Entry | Z | Borane (equiv) | Time (h) | % yield[b] | %1:%2[c] |
|---|---|---|---|---|---|
| 1 | F | HBPin (0.25) | 8 | 71 | 11:89 (8:92) |
| 2 | Cl | HBPin (0.25) | 36 | 76 | 80:20 (81:19) |
| 3 | Br | HBPin (0.25) | 48 | 73 | 95:5 (97:3) |
| 4 | I | B$_2$Pin$_2$ (1.0) | 40 | 70 | >99:1 (>99:1) |
| 5[d] | CH$_3$ | HBPin (0.25) | 72 | 64 | 94:6 (92:8) |
| 6 | OMe | HBPin (0.25) | 24 | 65 | 67:33 (67:33)[e] |
| 7[f] | SMe | B$_2$Pin$_2$ (0.25) | 18 | 55 | 90:10 (87:13)[e] |
| 8[d] | NMe$_2$ | B$_2$Pin$_2$ (1.0) | 72 | 58 | >99:1 (>99:1) |
| 9 | CO$_2$Me | B$_2$Pin$_2$ (0.8) | 48 | 65 | >99:1 (>99:1) |
| 10[g] | NHAc | B$_2$Pin$_2$ (1.6) | 18 | 62 | >99:1 (>99:1) |
| 11[h] | CF$_3$ | HBPin (1.1) | 24 | 68 | >99:1 (>99:1) |

[a]Unless otherwise noted, all reactions were run in THF solution at 25° C. with [Ir] = 3 mol %.
[b]Yields are for isolated products based on the limiting reagent.
[c]The major isomer was assigned by NMR and ratios were determined from crude reaction mixtures by GC integration. Isomer ratios for isolated products are in parentheses.
[d][Ir] = 6 mol %.
[e]Isomer ratio was determined from NMR integration.
[f]Reaction run at 80° C.
[g][Ir] = 8 mol %.
[h]Reaction run in n-hexane.

There are several approaches for evaluating steric effffects (White, D. P. et al., J. Org. Chem. 1999, 7707-7716). Following a course recommended by Ingold, (Ingold, C. K., J. Chem. Soc. 1932, 1032) Taft developed a parameter, $E_s$, to account for steric effects on hyrolysis and esterification rates of o-benzoate esters (Taft, R. W. J., J. Am. Chem. Soc. 1952, 74, 3120-3128). It was later shown that $E_s$ values could be quantitatively related to van der Waals radii, (Charlton, D., J. Am. Chem. Soc. 1969, 91, 615-618) and values have been calculated for substituents absent in Taft's original work (Kutter, E. et al., J. Med. Chem. 1969, 12, 647-652). Dubois later revised Taft's definition, introducing the Taft-Dubois steric paramater, $E'_s$ (Macphee, J. A. et al., Tetrahedron 1978, 34, 3553-3562). Despite their demonstrated utility, $E_s$ and $E'_s$ values are nonetheless empirical and the database of values is still limited. Alternatively, the energy difference between equatorial and axial conformers of monosubstituted cyclohexanes (the A value) has been invoked as a measure of steric effects (Winstein, S. et al., J. Am. Chem. Soc. 1955, 77, 5562-5578). Although the equatorial site is indeed favored from a steric standpoint, cyclohexane conformational energies are not immune to electronic effects. Hence, A values are poor predictors of steric differences for electronically disparate substituents. For our purposes, although there is no $E'_s$ value in the literature for CN, the $E_s$ value that is typically quoted places CN between F and Cl, which seems reasonable (Hansch, C. et al., Exploring QSAR: Hydrophobic Electronic, and Steric Constants; American Chemical Society: Washington, D.C., 1995; p. 227). Unfortunately, the value does not appear in the primary literature that is cited. A values are of little help as the value for CN is lower than that of F, (Jensen, F. R. et al., J. Am. Chem. Soc. 1969, 91, 344-351) and general agreement between A and $E_s$ values is poor.

Calculations of steric energies have been addressed using modern computational methods. We felt that a good, albeit crude, model for our purposes was that employed by Fujita and co-workers for evaluating the steric effects in the acid-catalyzed hydrolysis of o-benzamides (Sotomatsu, T. et al., J. Comput. Chem. 1991, 12, 135-138; and Sotomatsu, T. et al., J. Org. Chem. 1989, 54, 4443-4448). In essence, their approach involves calculating the difference in enthalpies for 2-substituted toluenes and tert-butylbenzenes relative to toluene and tert-butylbenzene to extract steric enthalpies, denoted as DDH$_s$(Z), for substituents Z, relative to hydrogen. For consistency, the dihedral angles for the methyl and tert-butyl groups were constrained as shown in Chart 1. Since CN and other substituents in Table 1 were not included in the previous report, we recalculated the series (AM1 calculations were carried out on an SGI Origin 3400 supercomputer using SPARTAN SGI Version 5.1.3, Wavefunction, Inc., Irvine, Calif.). Table 2 lists these DDH$_s$(Z) values along with calculated and experimental ratios of 2- and 3-borylated benzonitriles.

Chart 1

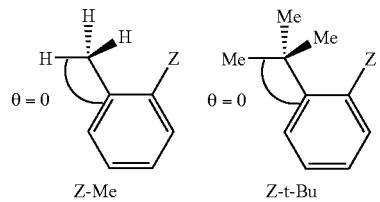

ΔΔH$_s$(Z) = [ΔH$_f$°(Z-t-Bu)-ΔH$_f$°(H-t-Bu)]
        -[ΔH$_f$°(Z-Me)-ΔH$_f$°(H-Me)]

TABLE 2

Calculated steric enthalpies (ΔΔH$_s$) for o-benzene substituents Z and isomer ratios for borylation.

| Z | ΔΔH$_s$(Z) kcal · mol$^{-1}$ | %1:%2 calc | %1:%2 observed |
|---|---|---|---|
| H | 0 | — | — |
| CN | 3.211 | — | — |
| F | 1.535 | 6:94 | 8:92 |
| Cl | 4.133 | 83:17 | 81:19 |
| Br | 5.405 | 98:2 | 97:3 |
| I | 7.759 | >99:1 | >99:1 |
| CH$_3$ | 5.532 | 98:2 | 92:8 |
| OMe | 2.013 | 31:69 | 67:33 |
| SMe | 3.682 | 66:34 | 87:13 |
| NMe$_2$ | 5.039 | 96:4 | >99:1 |
| CO$_2$Me | 4.856 | 94:6 | >99:1 |
| NHAc | 5.166 | 96:4 | >99:1 |
| CF$_3$ | 8.845 | >99:1 | >99:1 |

Agreement between the calculated and experimental isomer ratios is surprisingly good. The halide data correlates best, while selectivities for CO$_2$Me, NMe$_2$, and NHAc substituents are better than the calculated values. To gauge whether aromatic borylation is likely to be more sensitive to steric effects, it is instructive to consider putative transition states for acid-catalyzed hydrolysis of an o-benzamide (A) and Ir-catalyzed C—H activation (B) in Chart 2.

Chart 2

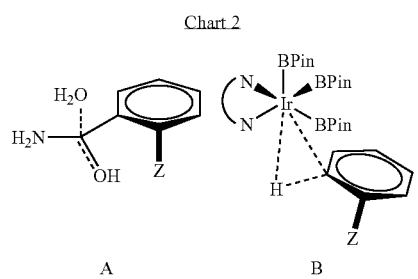

A       B

First, transition state A more closely resembles the steric model in Chart 1 from which DDH$_s$(Z) values are calculated. Moreover, transition state B should be more sensitive to the sterics of Z because an Ir—C bond ultimately forms ortho to Z, whereas attack by the less hindered water molecule is one carbon removed in transition state A.

The poorest agreement between calculated and observed isomer ratios in Table 2 is for Z=OMe, where the borylation is favored at the more hindered position. Although this could simply result from inherent deficiencies in the model, there is reason to believe electronic effects contribute to the regioselectivity. Specifically, while borylation of benzonitrile gives a nearly statistical 2.15:1 ratio of meta to para isomers, anisole borylation favors the meta isomer 4:1. After taking statistics into account, this corresponds to a 2:1 preference for meta vs. para borylation. Given that CN and OMe groups are nearly isosteric, the identical 2:1 preference for borylation meta to OMe may have electronic origins.

To strengthen what is a circumstantial case for sterics overriding electronics in borylations of 4-benzonitriles, we turned to 1,3-disubstituted CN and F benzenes, where C—H bonds flanked by 0-2 ortho hydrogens are present. Under DoM conditions, 1,3-dicyano and 1,3-difluorbenzene are known to react selectively at the 2-position as shown in Scheme 3 (Krizan, T. D. et al., J. Org. Chem. 1982, 47, 2681-2682; and Bennetau, B. et al., Tetrahedron 1993, 49, 10843-10854). If selectivities of Ir catalyzed borylations of CN and F substituted arenes are sterically directed, the propensity for borylation in the 1,3-disubstituted benzenes should follow the order 5->4->2-. As indicated in Scheme 3, this is indeed the case. Furthermore, only 1,3-difluorobenzene exhibits significant borylation at the 2-position, consistent with the lower steric requirement for F relative to CN. Murai has invoked CN to Ru Π-bonding to account for selective C—H activation ortho to CN (Kakiuchi, F. et al., Chem. Lett. 1999, 1083-1084). However, from the data in Scheme 3, the borylation ortho to H vs. CN is favored by a factor of 5.7 in the present system. Thus, sterically directed regioselectivity is the only satisfactory explanation for the regiochemistry in these borylations. Based on these results and the data in Table 2, we favor steric directing effects to account for the selectivities in Table 1.

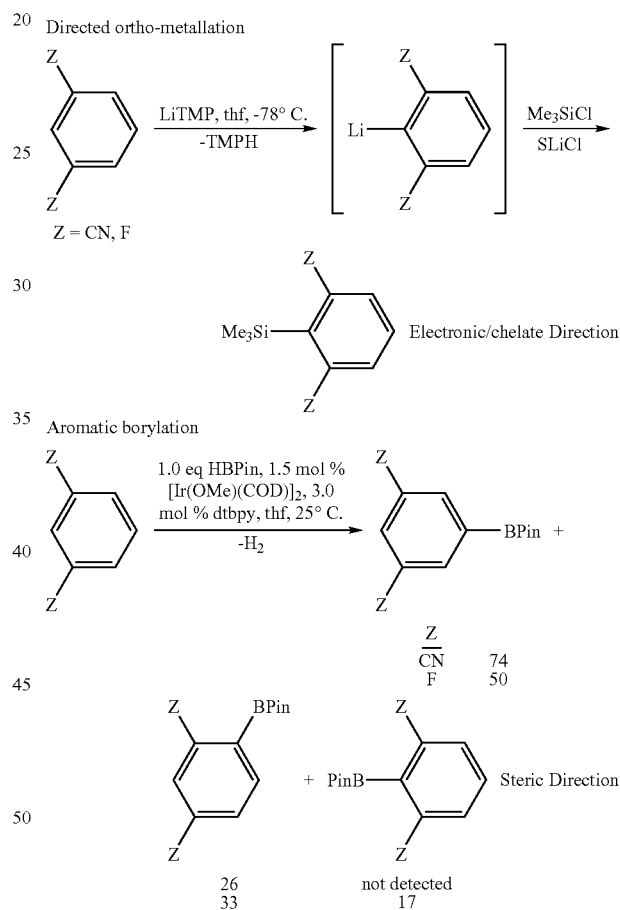

Scheme 3

Additional features of the reactions in Table 1 merit comment. First, the 2-borylated products for entries 2-11 are new compounds. In fact, 4-F-2-BPinC$_6$H$_3$CN is the only previously reported 2,4-benzonitrile with boron at the 2-position to the best of our knowledge (Blackaby, W. P. et al., U.S. Patent Publication No. 20040192692). Moreover, introduction of the BPin group using other methods, such as Miyaura's cross-coupling reactions of alkoxydiboron reagents and aryl halides, are inconvenient because access to the 2-halogenated compounds is extremely limited (Ishiyama, T. et al., J. Org. Chem. 1995, 60, 7508-7510). Entries 8-10 highlight the complementary nature of sterically directed borylations to DoM protocols, where hydrogens ortho to amine, ester, and amide groups react preferentially (Clayden, J. et al., Tetrahedron Lett. 2003, 44, 3059-3062; and Jaroch, S. et al., Bioorg. Med. Chem. Lett. 2002, 12, 2561-2564). Thus, aromatic borylation provides the most general approach to elaborating the 2 positions of 4-substituted benzonitriles. Lastly, it should be noted that entries 7 and 10 are the first examples of functional group tolerance for SMe and NHAc substituents, respectively.

The regioselectivities in Table 2 are not necessarily limited to disubstituted benzenes. In addition to diborylation of 4-benzonitriles (vide infra), we also note that 4-bromo-2-fluorobenzonitrile is borylated according to Eq 1, affording a 5:95 ratio of 5- and 6-borylated products. This is a particularly attractive reaction because 1,2-benzisoxazoles and other heterocycles can be obtained by substitution of fluoride followed by ring-forming condensation with the cyano group (Cui, J. R. et al., Bioorg. Med. Chem. Lett. 2002, 12, 2925-2930). Similarly, borylation of 3,4-dichlorobenzonitrile yields the 5- and 6-borylated isomers in a 20:80 ratio. For both substrates, the selectivity for borylation ortho to CN vs. halide is virtually identical to that for the corresponding 4-halobenzonitriles in Table 1.

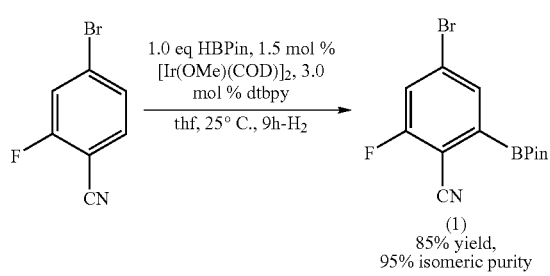

In order to avoid diborylation, excess arene was used for several entries in Table 1. We were curious as to how efficiently the diborylated products could be formed and whether compounds with isomeric purities sufficiently high as to be synthetically useful could be obtained. The reactions were typically run in THF with a 4:1 ratio of HBPin to arene at twice the catalyst loading for monoborylation. The results are given in Table 3.

TABLE 3

Diborylations of 4-benzonitriles.[a]

| Z | % yield, time | Products[b] | |
|---|---|---|---|
| F | 92, 24 h | (F, BPin, PinB, CN) 46% (14%) | (F, PinB, BPin, CN) 54% (86%) |
| OMe | 81, 48 h[c] | (OMe, BPin, PinB, CN) 80% (60%) | (OMe, PinB, BPin, CN) 20% (33%) |
| Cl | 82, 48 h | (Cl, BPin, PinB, CN) 80% (44%) | (Cl, PinB, BPin, CN) 20% (54%) |
| CN | 71, 20 h[d] | (CN, BPin, PinB, CN) | |
| CF3 | 83, 36 h | (CF3, PinB, BPin, CN) | |

[a]Unless otherwise noted, all reactions were run in THF solution at 25° C. with 4.0 eq HBPin and [Ir] = 6 mol %.
[b]Isomer distribution determined GC-FID. Calculated values are shown in parentheses. For Z = OMe and Cl, the 3,5-diborylation product are calculated as 7% and 2% of the isomer mixture.
[c]Reaction run at 60° C.
[d]Isolated as a single isomer after recrystallization from a 93:7 mixture of 2,5- and 2,6-borylated isomers.

Unlike the situation for 4-bromo-2-fluorobenzonitrile and 3,4-dichlorobenzonitrile, the observed distribution of isomers is much different than a simple extrapolation of selectivities from Table 1 predicts Isomer distributions for diborylation where the BPin group does not affect selectivity were calculated as follows. For 4-chlorobenzonitrile, borylation ortho to CN vs. Cl is favored by a factor of 4, giving the 2-borylated isomer as the major product. In the second borylation, selectivity ortho to CN is lowered by half because there are two H's ortho to Cl and only one H ortho to CN in the monoborylated product. Applying analogous aruguments to the other monoborylated isomer, the percentages of 2,6-,2,5-, and 3,5-diborylated isomers can be calculated as 54%, 44% and 2%, respectively. Isomer ratios for the other substrates in Table 3 were calculated similarly. In all cases the extent of 2,5-diborylation is significantly higher than expected, except for Z=CF3 where borylation ortho to CF3 is likely prohibitive.

The data suggest that the BPin group has a directing role. To answer this question, we examined the regioselectivity for PhBPin borylation in THF under similar reaction conditions (Eq 2). The reaction was examined at low conversion to avoid skewing the data by borylation of m-$C_6H_4$(BPin)$_2$. The experiment in Eq 2 was performed through the reaction of benzene with 1.2 equivalents of HBPin in the presence of Ir catalyst. The first equivalent of borane generates the PhBPin in situ and the remaining 0.2 equivalents give the diborylated isomers. The para to meta ratio is 1.8:1, significantly greater than the 1:2 statistical ratio. This translates to a 3.6:1 selectivity for para vs. meta borylation after statistical corrections. While we are reluctant to speculate on the origins of this selectivity, BPin clearly has a para directing effect that likely contributes to the regioselectivities in Table 3. Lastly, it should be noted that single isomers of diborylated products can readily be obtained for Z=CN, or $CF_3$.

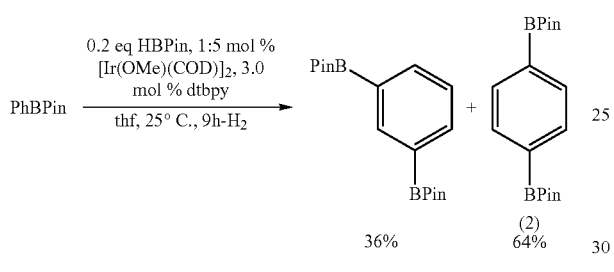

We have also examined a limited number of heteroaromatic compounds to assess whether the regioselectivities found for arenes will translate to other substrates (Scheme 4). Borylation of 1,5-dimethyl-2-pyrrolecarbonitrile (3a) gives an 85:15 ratio of the regioisomers 4a and 5a with the major isomer 4a arising from borylation adjacent to the cyano group. Similarly, 5-methyl-2-furonitrile (3b) borylates predominantly at the 3-position to also give an 85:15 ratio of borylated isomers 4b and 5b. Borylation of 2-bromo-5-cyanothiophene was unsuccessful. Since the steric interactions between adjacent positions diminish as aromatic rings contract, the decline in selectivity for the 5-membered heterocycles is not surprising. Two isomeric cyanopyridines were also examined. 5-bromo-2-cyanopyridine undergoes borylation to afford an isomer mixture. While borylation ortho to CN accounts for the major product, the degree of borylation ortho to Br is substantially higher than that found for 4-bromobenzonitrile. Somewhat surprisingly, 2-bromo-5-cyanopyridine gave no borylation products. Since halogen substituted aromatic heterocycles tend to be more reactive than their carbocyclic counterparts, side reactions that deactivate catalytically active species are more likely.

Scheme 4

Conclusions

In summary, the steric directing effects that govern the regioselectivities in Ir catalyzed borylations of aromatic and heteroaromatic compounds enable functionalization of C—H bonds adjacent to cyano groups, when these positions are the least hindered sites in the substrate. The regioselectivities for borylations complement those found in electrophilic aromatic substitutions and DoM's, and several relatively simple borylated products have been prepared for the first time. Diborylations of 4-benzonitriles favor para-disposed BPin groups when borylation at the 5-position is possible. Similar trends in regioselectivities can be extended to borylations of heteroaromatic nitriles, the substrate scope is narrower and the regioselectivity is poorer than for carbocyclic aromatic substrates. Regioselectivities were improved by modifying the Ir ligands, as well as sterically differentiating other aromatic substituents.

Methods:

Pinacolborane (HBPin) and bis($\eta^4$-1,5-cyclooctadiene)-di-$\mu$-methoxy-diiridium(I) {Ir(OMe)(COD)}$_2$ were prepared per literature procedures (Knochel, P.; Davidson, J.; Tucker, C. E., J. Org. Chem. 1992, 57, 3482-3485 and Uson, R.; Oro, L. A., Inorg. Synth. 1985, 23, 126-130). Bis(pinacolato)diboron ($B_2Pin_2$) was purchased from Callery Chemical Company and was used without purification. Tris(dibenzylidineacetone)dipalladium(0) ($Pd_2dba_3$) was purchased from Strem. 4,4'-Di-t-butyl-2,2'-bipyridine (d$^t$bpy), tricyclohexylphosphine, and potassium acetate were purchased from Aldrich. 1-Bromo-3,5-difluorobenzene, 2-bromo-1,3-difluorobenzene, 1-bromo-2,4-difluorobenzene, and 4-iodobenzonitrile were purchased from Alfa Aesar. 4-Bromobenzonitrile and 4-methoxybenzonitrile were purchased from Lancaster Synthesis. 2-Bromo-4-methylbenzonitrile was purchased from Trans World Chemicals. 5-Bromo-2-cyanopyridine and 2-bromo-5-cyanopyridine were purchased from Matrix Scientific. All other benzonitriles were purchased from Aldrich. All substrates were purified before use. Solid substrates were sublimed under vacuum. 5-Methyl-2-furonitrile and 5-bromothiophene-2-carbonitrile were passed through activated alumina. 1,4-Dioxane and n-hexane were refluxed over sodium, distilled, and degassed. Tetrahydrofuran was used from a dry still packed with activated alumina. Silica gel was purchased from EM Science (230-400 Mesh).

Unless otherwise specified, all reactions were carried out at 25° C. in 20 mL vials in a glove box under a nitrogen atmosphere. All reactions were monitored by a Varian CP-3800 GC-FID (column type: WCOT Fused silica 30 m×0.25 mm ID coating CP-SIL 8 CB). GC-FID method: 70° C., 2 min.; 20° C./min, 9 min.; 250° C., 20 min.; 1.8 mL/min flow rate. All reported yields are for isolated materials.

$^1$H and $^{13}$C NMR spectra were recorded on a Varian Inova-300 (300.11 and 75.47 MHz respectively), Varian VXR-500, or Varian Unity-500-plus spectrometer (499.74 and 125.67 MHz respectively) and referenced to residual solvent signals. $^{11}$B spectra were recorded on a Varian VXR-300 operating at 96.29 MHz and were referenced to neat $BF_3.Et_2O$ as the external standard. $^{19}$F spectra were recorded on a Varian Inova-300 operating at 282.36 MHz and were referenced to neat $CFCl_3$ as the external standard. All coupling constants are apparent J values measured at the indicated field strengths. All 1-dimensional NOE experiments were obtained using the Varian implementation of the DPFGSE-NOE experiment (hereafter termed NOESY1D). All 2-dimensional experiments were run using z-axis pulse field gradients. Elemental analyses were performed at Michigan State University using a Perkin Elmer Series II 2400 CHNS/O Analyzer. GC-MS data were obtained using a Varian Saturn 2200 GC/MS (column type: WCOT Fused silica 30 m×0.25 mm ID coating CP-SIL 8 CB). High-resolution mass spectra were obtained at the Michigan State University Mass Spectrometry Service Center with a JOEL-AX505 mass spectrometer (resolution 7000). Melting points were measured on a MEL-TEMP® capillary melting apparatus and are uncorrected.

General Procedure

Substrates which gave a significant amount of both isomers were borylated employing an excess of benzonitrile to minimize diborylation (General procedure A), otherwise, excess borane was employed (General procedure B). Unless otherwise specified, all reactions were run in THF solutions at 25° C. with 3 mol % [Ir]. The major isomer for the borylation of 4-methylbenzonitrile was identified by preparing an authentic sample using a slightly modified literature procedure. The regioisomers in all other cases were assigned by NMR spectroscopy ($^{13}$C for substrates which have fluorine, while gHMBC and NOESY1D were used for substrates without fluorine). Ratios of the major versus minor isomer were determined from the crude reaction mixtures. Yields are based on the limiting reagent.

General Procedure A (Borane as Limiting Reactant):

In a glove box, a 20 mL vial, equipped with a magnetic stirring bar, was charged with {Ir(OMe)(COD)}$_2$ (5.0 mg, 0.0075 mmol, 3 mol % Ir), 4,4'-di-t-butyl-2,2'-bipyridine (d$^t$-bpy) (4.0 mg, 0.015 mmol, 3 mol %), and pinacolborane (HBPin) (73 µL, 64 mg, 0.5 mmol, 1 equivalent). These reagents were dissolved in 2 mL of THF, the corresponding benzonitrile (2 mmol, 4 equivalents) was added, and the mixture was stirred at room temperature until the reaction was judged complete by GC-FID. Solvent was removed under reduced pressure. The crude material was dissolved in $CH_2Cl_2$ and passed through a plug of silica gel to remove metal byproducts. Kugelrohr distillation gave analytically pure samples.

General Procedure B (Benzonitrile as Limiting Reactant):

In a glove box, a 20 mL vial, equipped with a magnetic stirring bar, was charged with {Ir(OMe)(COD)}$_2$ (10 mg, 0.015 mmol, 3 mol % Ir), d$^t$bpy (8.1 mg, 0.03 mmole, 3 mol %), and excess HBPin or B$_2$Pin$_2$ (1.1 to 3.2 equivalents of boron). These reagents were dissolved in 3 mL of THF, the corresponding benzonitrile (1 mmol, 1 equivalent) was added, and the mixture was stirred at room temperature until the reaction was judged complete by GC-FID. Solvent was removed under reduced pressure. The crude material was dissolved in $CH_2Cl_2$ and passed through a plug of silica gel to furnish the desired borylated product.

General Procedure C (Diborylation):

In a glove box, a 20 mL vial, equipped with a magnetic stirring bar, was charged with {Ir(OMe)(COD)}$_2$ (20 mg, 0.03 mmol, 6 mol % Ir), d$^t$bpy (16.1 mg, 0.06 mmol, 6 mol %), and excess HBPin (4 equivalent of boron). These reagents were dissolved in 3 mL of THF, the corresponding benzonitrile (1 mmol, 1 equivalent) was added, and the mixture was stirred at room temperature until the reaction was judged complete by GC-FID. Solvent was removed under reduced pressure. The crude material was dissolved in $CH_2Cl_2$ and passed through a plug of silica gel to furnish the desired borylated product.

Regioisomer Assignment by NMR Spectroscopy:

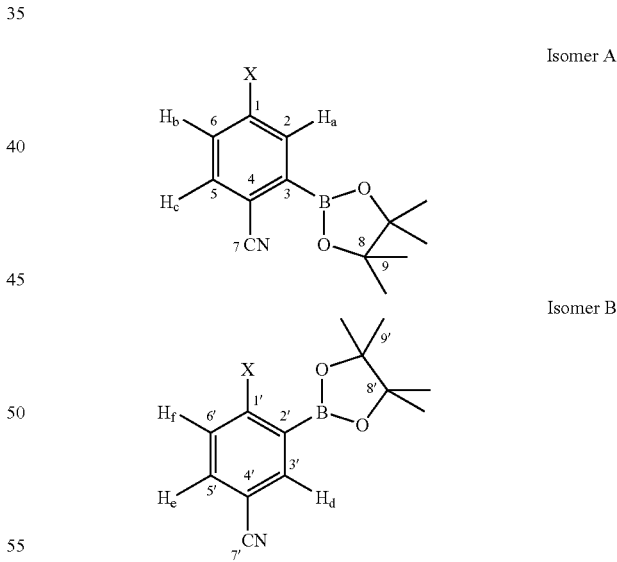

Isomer A

Isomer B

Figure 2:
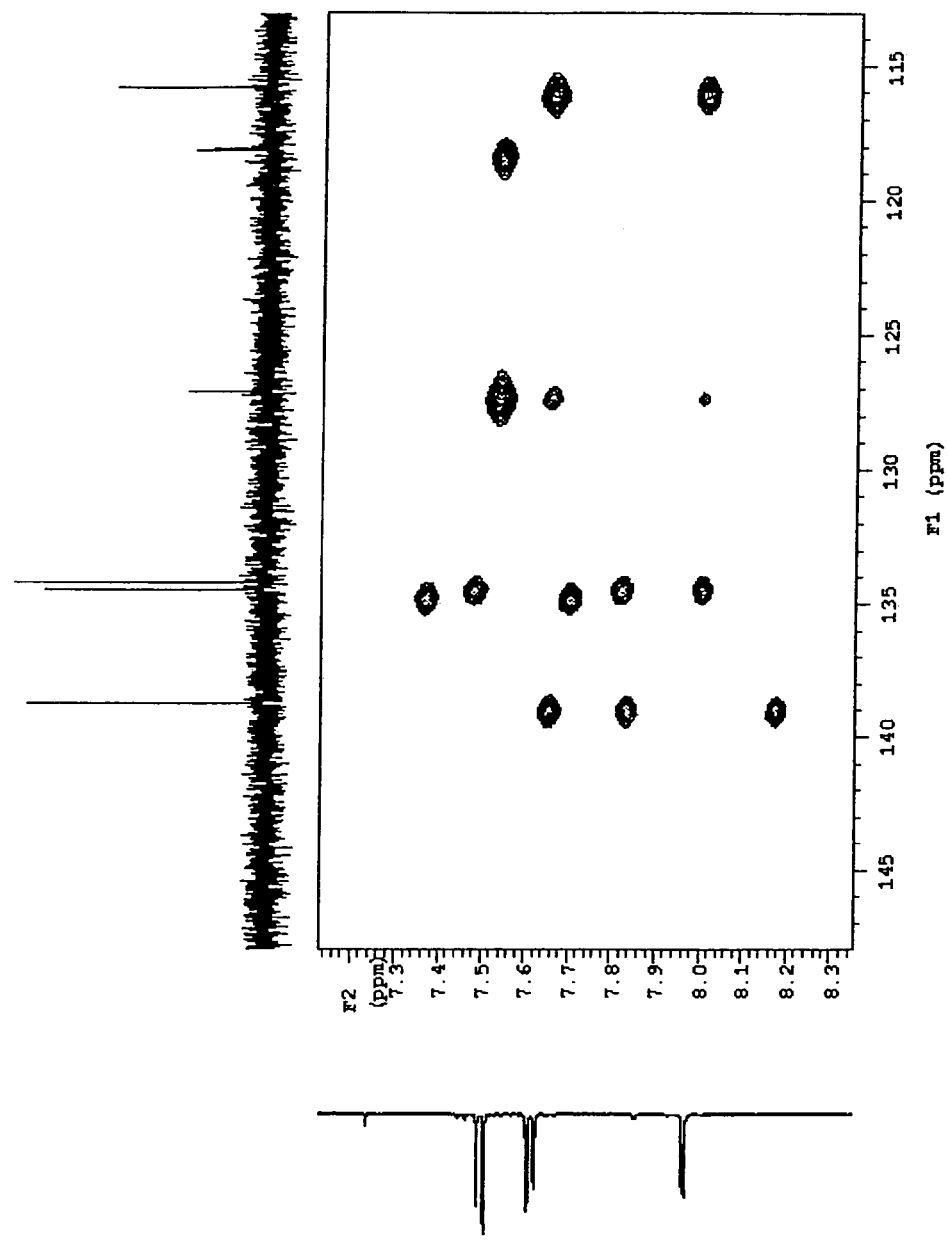
FIG. 2 is a gHMBC spectrum of the borylation products of 4-bromobenzonitrile.
Figure 3:
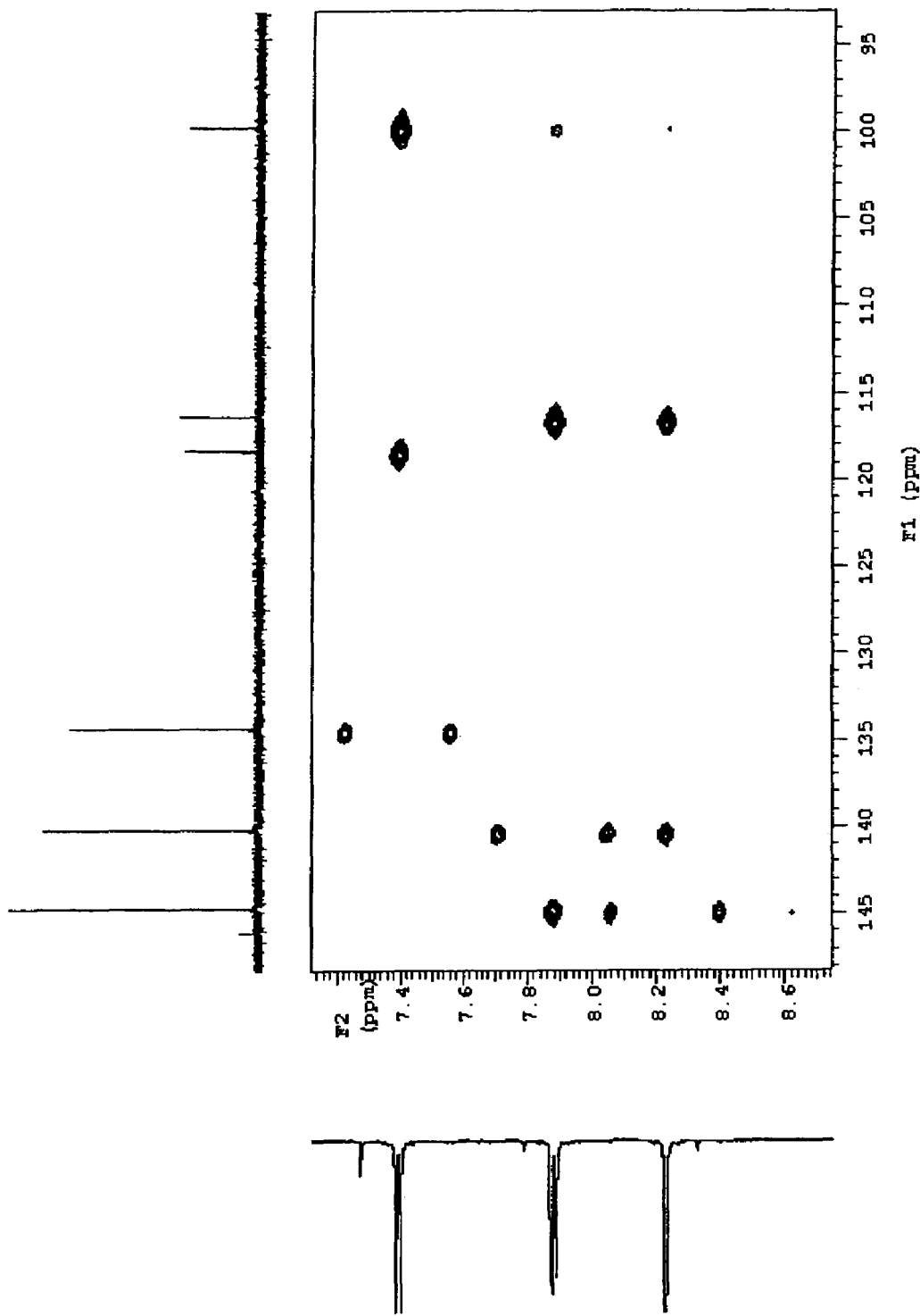
FIG. 3 is a gHMBC spectrum of the borylation product of 4-iodobenzonitrile.
Figure 4:
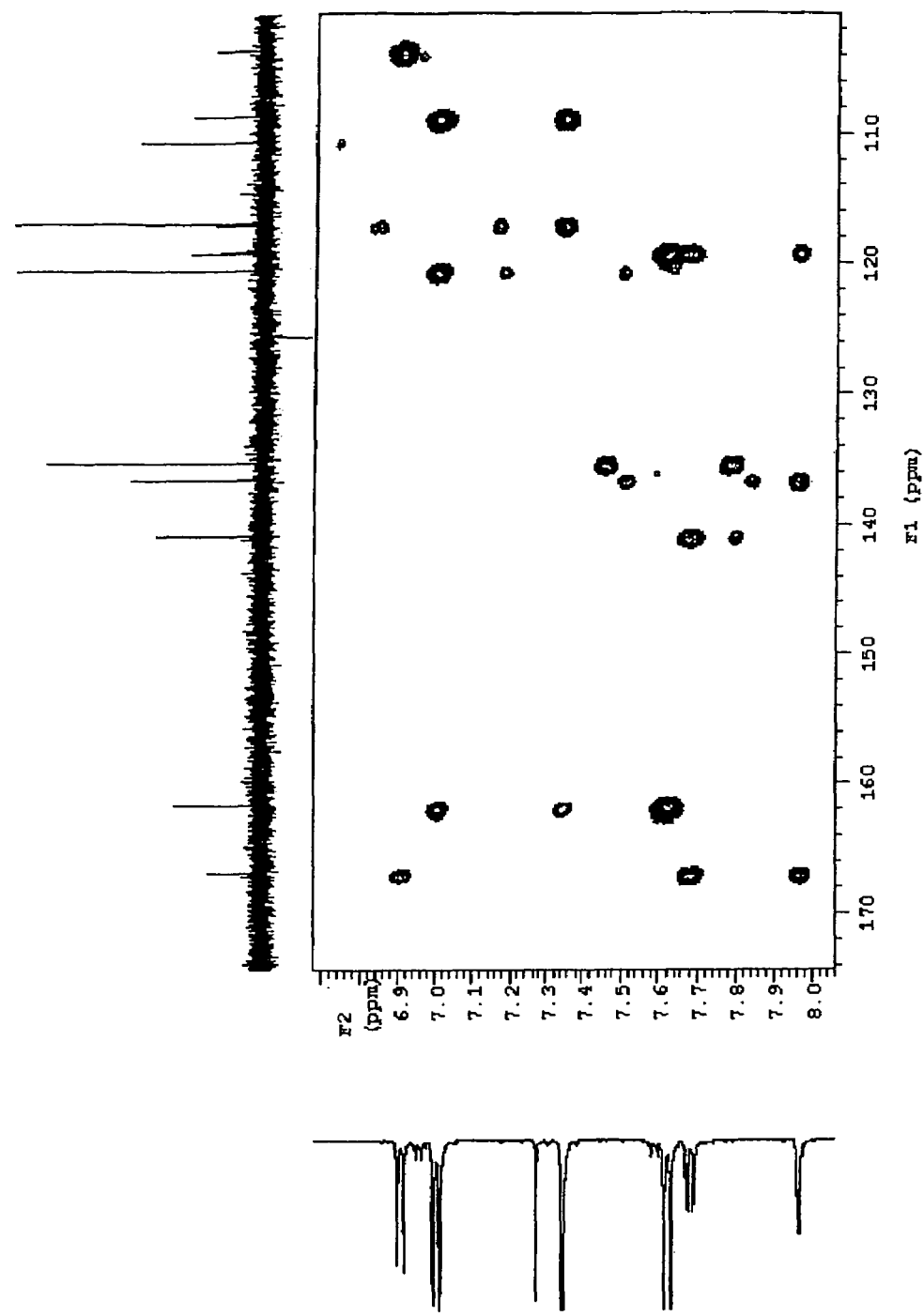
FIG. 4 is a gHMBC spectrum of the borylation products of 4-methoxybenzonitrile.
Figure 5:
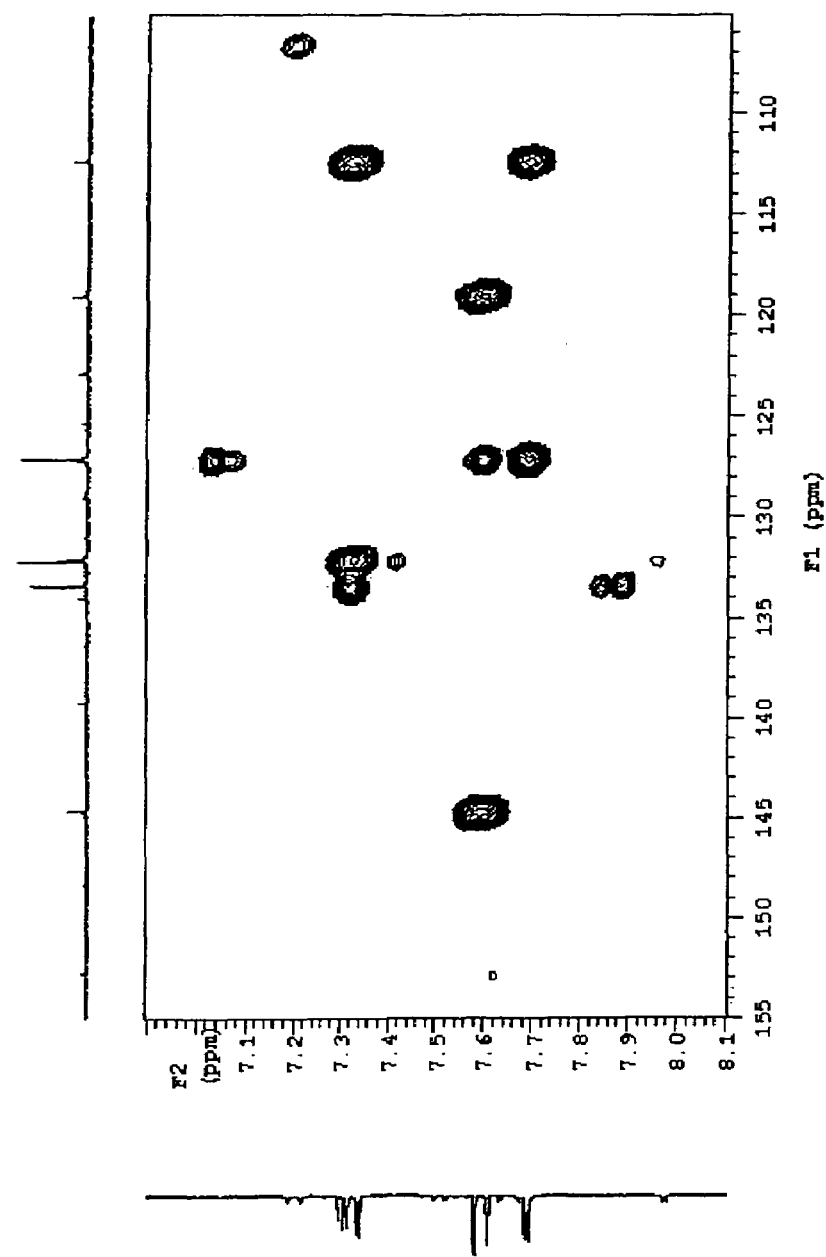
FIG. 5 is a gHMBC spectrum of the borylation products of 4-thiomethylbenzonitrile.
Figure 6:
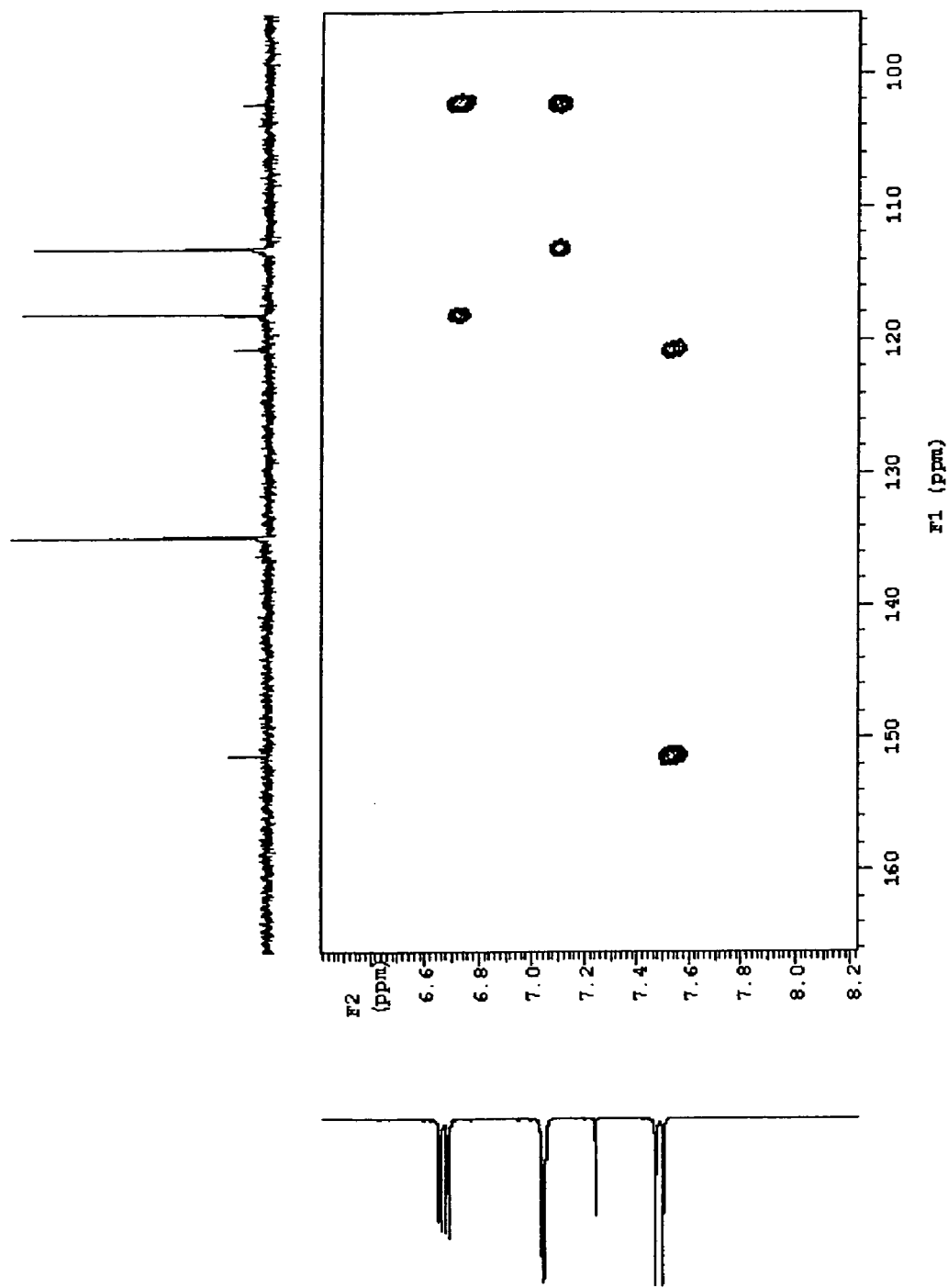
FIG. 6 is a gHMBC spectrum of the borylation product of 4-dimethylaminobenzonitrile.
Figure 7:
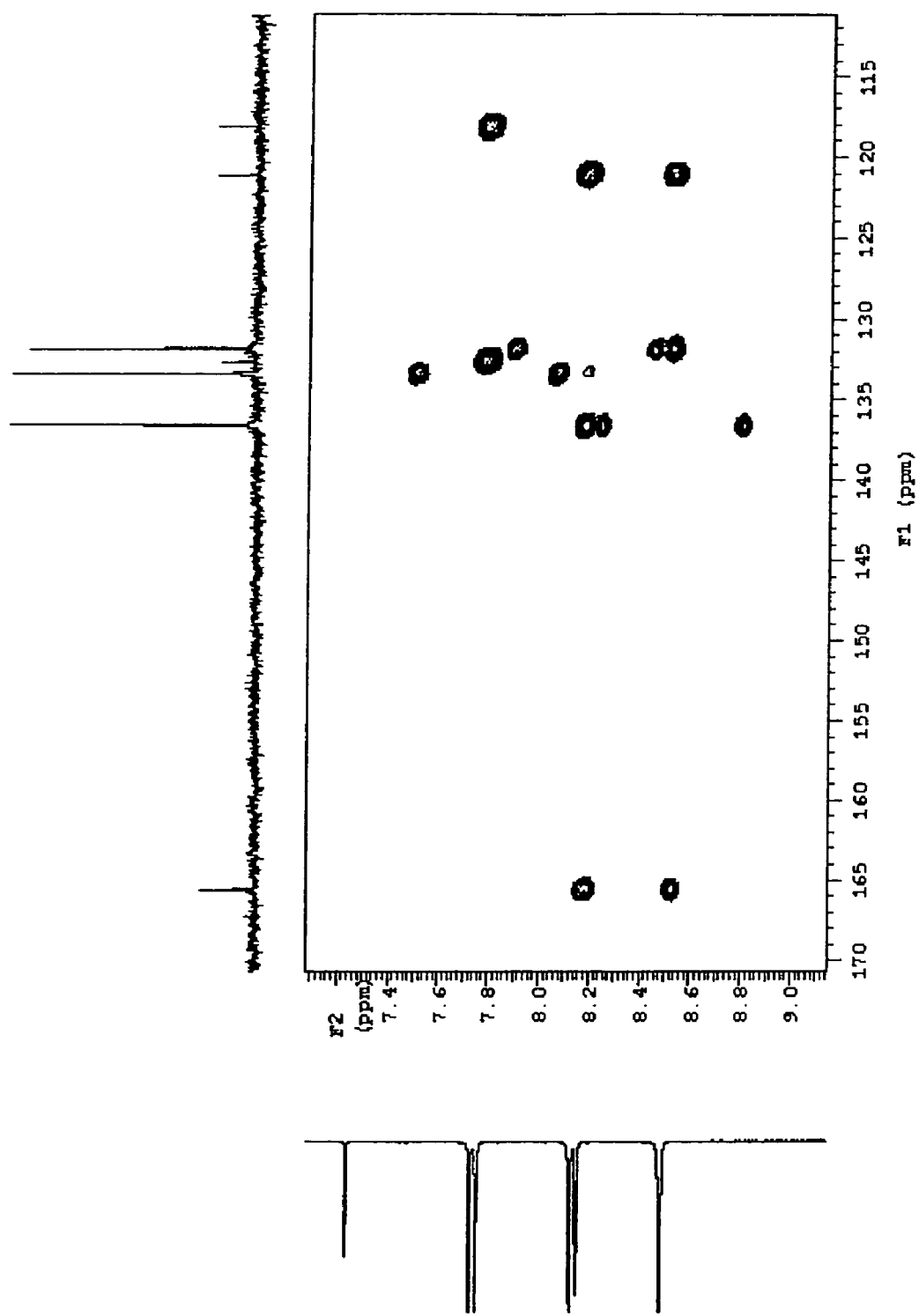
FIG. 7 is a gHMBC spectrum of the borylation product of methyl 4-cyanobenzoate.
Figure 8:
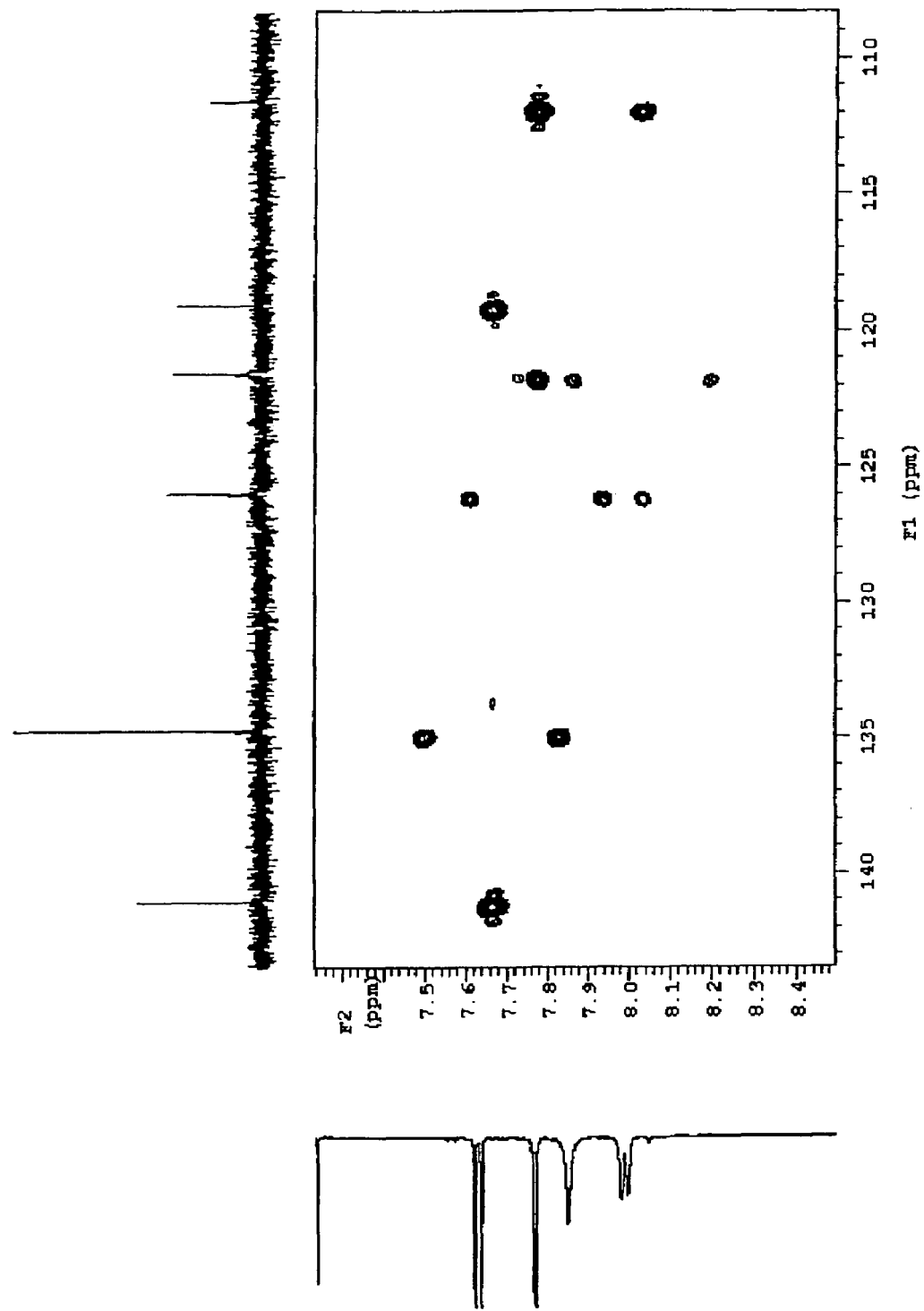
FIG. 8 is a gHMBC spectrum of the borylation product of 4'-cyanoacetanilide.
Figure 9:
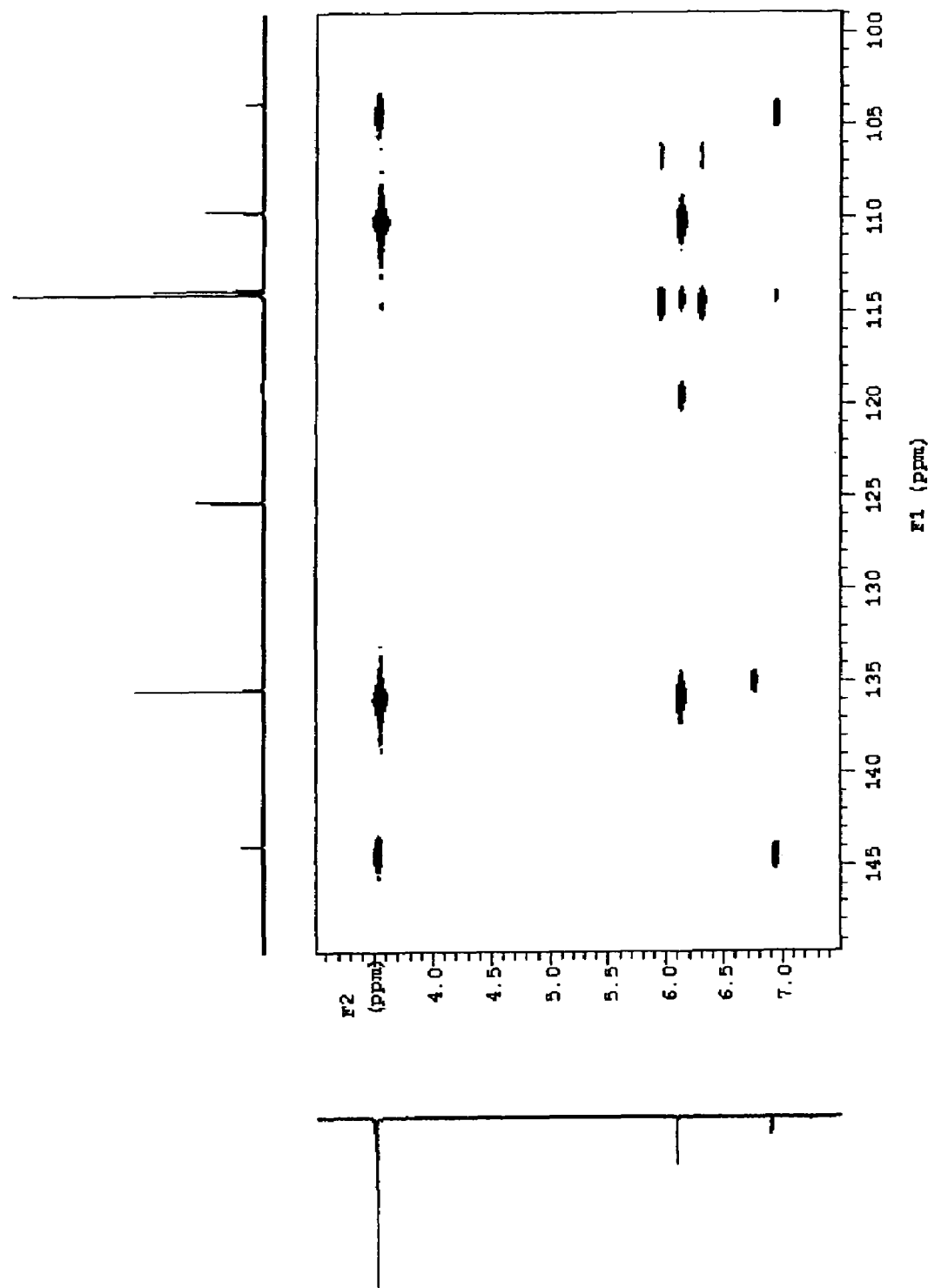
FIG. 9 is a gHMBC spectrum of the borylation products of 1,5-dimethyl-2-pyrrolecarbonitrile.
Figure 10:
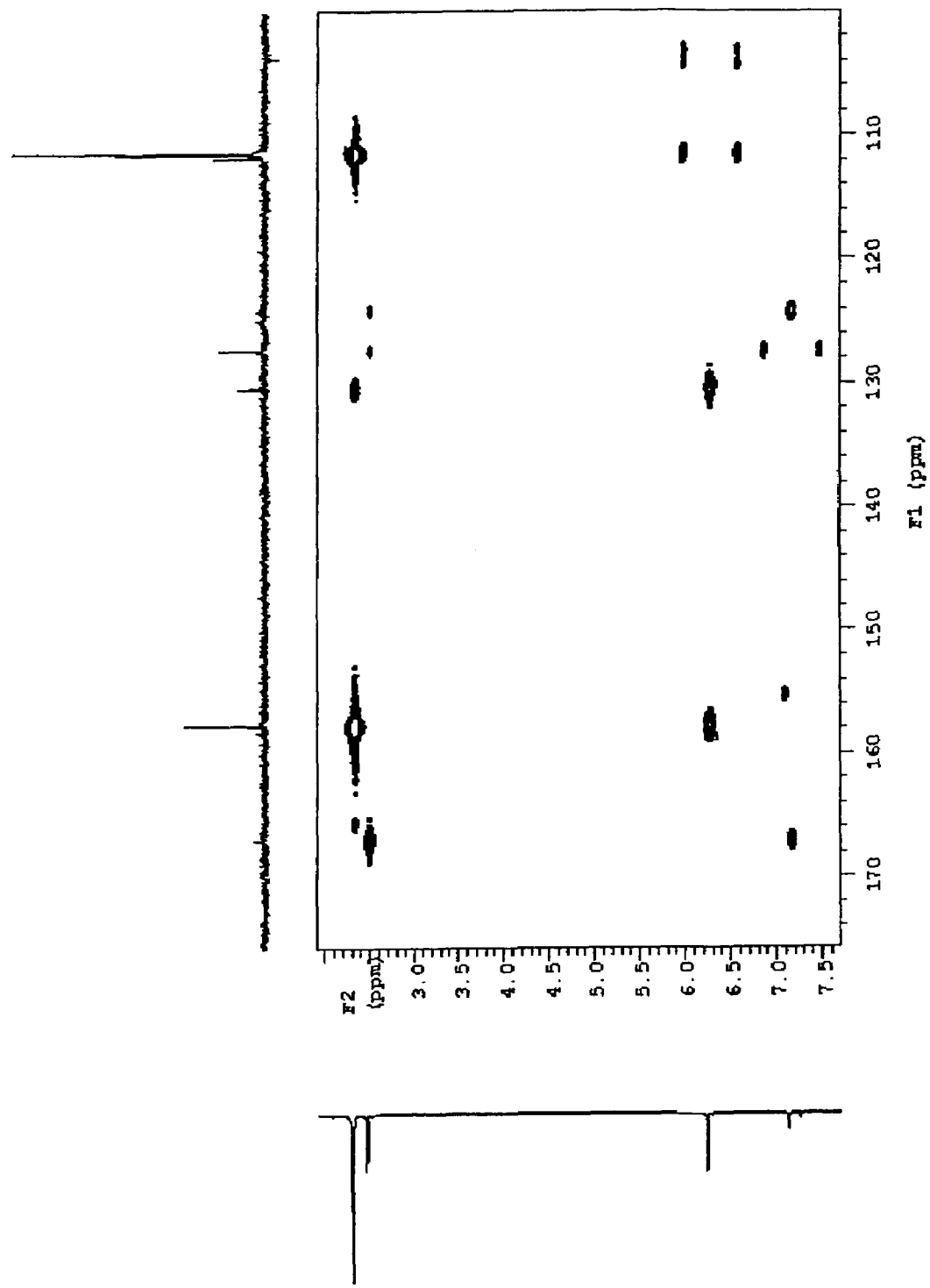
FIG. 10 is a gHMBC spectrum of the borylation products of 5-methyl-2-furonitrile.

From gHMBC NMR experiments, the two regioisomers for the borylation of 4-substituted benzonitriles can be distinguished unambiguously as in FIGS. 1 to 10. In isomer A, carbon atoms represented as C1 and C4 on the benzene ring, as well as C7 (nitrile carbon) are the three quaternary carbon atoms in the 100-170 ppm region (quaternary carbon C3 is typically not observed due to broadening from and coupling with boron). These three quaternary carbon atoms should show cross peaks due to long range H—C couplings ($^3J_{C-H}$), which can be observed using gHMBC spectroscopy. In the gHMBC spectrum, carbon atoms C1 and C7 should show one cross peak each to proton $H_c$, whereas carbon atom C4 should show two cross peaks to protons $H_a$ and $H_b$. Therefore the resulting number of cross peaks for C1, C4, and C7 should be 1, 2, and 1, respectively.

In Isomer B, carbon atoms represented as C1', C4', on the benzene ring, as well as C7' (nitrile carbon) are the three quaternary carbon atoms in the 100-170 ppm region (quaternary carbon C2' is typically not observed due to broadening from and coupling with boron). These three quaternary carbon atoms should show cross peaks due to long range H—C couplings ($^3J_{C\text{-}H}$). In the gHMBC spectrum, carbon atoms C1' and C7' should show two cross peaks each, to protons $H_d$ and $H_e$, whereas carbon atom C4' should show only one cross peak to proton $H_f$. Therefore the resulting number of cross peaks for C1', C4', and C7' should be 2, 1, and 2, respectively. Hence isomers A and B can be unambiguously assigned from gHMBC data.

For isomer A, with proton $H_c$ unambiguously assigned by gHMBC, $H_a$ and $H_b$ can be assigned from their multiplicities. Proton $H_a$ appears as a doublet, coupled to proton $H_b$ with J≈2-3 Hz. Proton $H_b$ appears as a doublet of doublets due to coupling to protons $H_a$ and $H_c$. Carbon atoms C2, C6, and C5 were then assigned from the correlations in the gHMQC spectra. Carbon atom C7 (nitrile carbon) usually appears around δ 119. Depending on the substituent, carbon atom C1 was usually found shifted downfield around δ 130-170 (except in 4-iodobenzonitrile for which it appears around δ 100). Carbon atom C4 is shifted upfield, and was usually found around δ 100-115. Similarly, all the carbons of isomer B can be assigned.

In the five membered heterocycles, the $^4J_{H\text{-}H}$ coupling was used together with gHMBC and NOESY1D spectroscopy to identify the major isomer. Regioisomers in the fluorine containing benzonitriles were assigned by $^{13}C$ spectroscopy (with the help of the fact that the boron bearing carbon is not observed due to broadening from and coupling with boron). In the case of 1,3-dicyanobenzene, $^1H$ NMR spectroscopy was employed to assign the major and minor isomers.

Experimental Details and Spectroscopic Data

EXAMPLE 1

Borylation of 4-fluorobenzonitrile

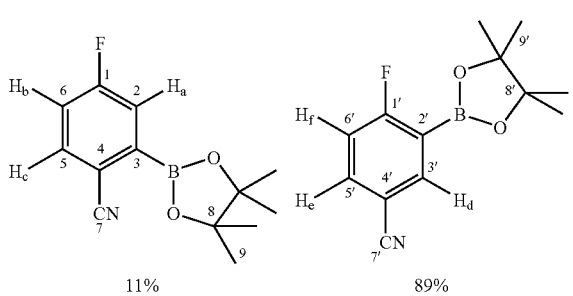

General procedure A was applied to 4-fluorobenzonitrile (242 mg, 2 mmol) and HBPin (73 μL, 64 mg, 0.5 mmol) with a reaction time of 8 h. The ratio of the two isomers in the crude reaction mixture by GC was 11:89. Kugelrohr distillation furnished a mixture of the two isomeric borylated products (88.5 mg, 72%) as a white solid. The ratio of the two isomers in the isolated product by GC was 8:92. $^{13}C$ NMR spectroscopy was used to assign the major isomer as 4-fluoro-3-(4,4,5,5-tetramethyl-1,3,2-dioxaboryl)benzonitrile. $^1H$ NMR (CDCl$_3$, 500 MHz): δ (major isomer) 8.04 (dd, $^4J_{H\text{-}F}$=5.4 Hz, J=2.2 Hz, 1H, $H_d$), 7.7 (ddd, J=8.5, 2.2 Hz, $^4J_{H\text{-}F}$=4.9 Hz, 1H, $H_e$), 7.1 (t, J=8.5 Hz, 1H, $H_f$), 1.32 (br s, 12H), (minor isomer) 7.67 (dd, J=8.8 Hz, $^4J_{H\text{-}F}$=4.9 Hz, 1H, $H_c$), 7.52 (dd, $^3J_{H\text{-}F}$=8.5 Hz, J=2.9 Hz, 1H, $H_a$), 7.17 (dt, J=8.3, 2.9 Hz, 1H, $H_b$) 1.34 (br s, 12H); $^{13}C$ NMR {$^1H$} (CDCl$_3$, 125 MHz): δ (major isomer) 169.0 (d, $^1J_{C\text{-}F}$=261.3 Hz, C1'), 141.6 (d, $^3J_{C\text{-}F}$=9.6 Hz, C3'), 137.0 (d, $^3J_{C\text{-}F}$=10.5 Hz, C5'), 117.9 (nitrile C7'), 116.7 (d, $^2J_{C\text{-}F}$=25.6 Hz, C6'), 108.2 (d, $^4J_{C\text{-}F}$=3.8 Hz, C4'), 84.5 (C8'), 24.7 (C9'), (minor isomer) 164.2 (d, $^1J_{C\text{-}F}$=257.1 Hz, C1), 135.9 (d, $^3J_{C\text{-}F}$=8.8 Hz, C5), 122.8 (d, $^2J_{C\text{-}F}$=21.0 Hz, C2), 118.5 (d, $^2J_{C\text{-}F}$=22.2 Hz, C6), 118.1 (nitrile C7), 113.1 (C4), 85.1 (C8), 24.7 (C9); $^{11}B$ NMR (CDCl$_3$, 96 MHz): δ 29.92; $^{19}F$ NMR (CDCl$_3$, 282 MHz): δ (major isomer) -92.62 (m), (minor isomer) -104.84 (m); FT-IR (neat): 3076, 2982, 2934, 2231, 1608, 1487, 1429, 1412, 1373, 1350, 1236, 1143, 1070, 964, 852, 835, 571 cm$^{-1}$; LRMS (% rel. int.): m/e (major isomer) 247 M$^+$ (26), 232 (100), 205 (12), 188 (20), (minor isomer) 247 M$^+$ (29), 232 (97), 206 (100), 189 (74), 148 (97), 121 (25); Anal. Cacld for C$_{13}$H$_{15}$BFNO$_2$: C, 63.20; H, 6.12; N, 5.67. Found: C, 63.52; H, 6.20; N, 5.56. HRMS Calcd for C$_{13}$H$_{15}$BFNO$_2$: 247.1180. Found: 247.1171.

EXAMPLE 2

Borylation of 4-chlorobenzonitrile

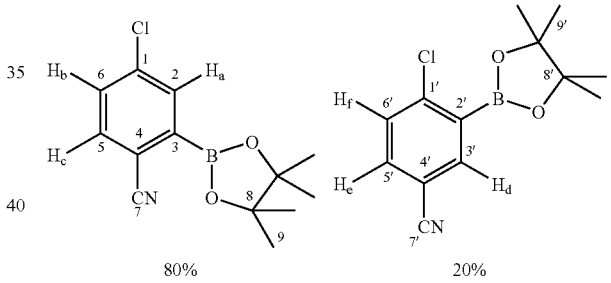

General procedure A was applied to 4-chlorobenzonitrile (550.3 mg, 4 mmol) and HBPin (145 μL, 128 mg, 1 mmol) with a reaction time of 36 h. The ratio of the two isomers in the crude reaction mixture by GC was 80:20. Kugelrohr distillation furnished a mixture of the two isomeric borylated products (200 mg, 76%) as a white solid. The ratio of the two isomers in the isolated product by GC was 81:19. gHMBC spectroscopy (FIG. 1) was used to assign the major isomer as 4-chloro-2-(4,4,5,5-tetramethyl-1,3,2-dioxaboryl)benzonitrile. $^1H$ NMR (CDCl$_3$, 300 MHz): δ (major isomer) 7.80 (d, J=2.2 Hz, 1H, $H_a$), 7.57 (d, J=8.3 Hz, 1H, $H_c$), 7.45 (dd, J=8.3, 2.2 Hz, 1H, $H_b$), 1.33 (br s, 12H), (minor isomer) 7.94 (d, J=2.2 Hz, 1H, $H_d$), 7.56 (dd, J=8.3, 2.2 Hz, 1H, $H_e$), 7.41 (d, J=8.3 Hz, 1H, $H_f$), 1.32 (br s, 12H); $^{13}C$ NMR {$^1H$} (CDCl$_3$, 75 MHz): δ (major isomer) 138.5 (C1), 135.8 (C2), 134.5 (C5), 131.2 (C6), 118.0 (nitrile C7), 115.3 (C4), 85.0 (C8), 24.6 (C9), (minor isomer) 144.5 (C1'), 140.1 (C3'), 134.6 (C5'), 130.2 (C6'), 117.8 (nitrile C7'), 110.2 (C4'), 84.7 (C8'), 24.6 (C9'); $^{11}B$ NMR (CDCl$_3$, 96 MHz): δ 29.59; FT-IR (neat): 2982, 2228, 1587, 1554, 1479, 1402, 1373, 1333, 1271, 1215, 1169, 1144, 1103, 1065, 1042, 965, 870, 847, 831 cm$^{-1}$; LRMS (% rel. int.): m/e (major isomer) 263 M$^+$ (24), 248 (65), 222 (100), 205 (31), 164 (32), 137 (11), (minor isomer) 263 M⁺ (1), 248 (27), 228 (100), 186 (60), 164 (15), 142 (6); Anal. Calcd for $C_{13}H_{15}BClNO_2$: C, 59.25; H, 5.74; N, 5.32. Found: C, 58.90; H, 5.74; N, 5.10.

EXAMPLE 3

Borylation of 4-Bromobenzonitrile

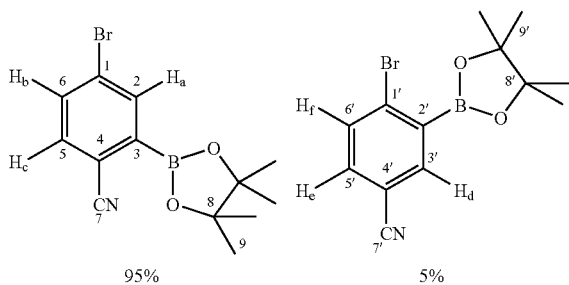

95%    5%

General procedure A was applied to 4-bromobenzonitrile (364.1 mg, 2 mmol) and HBPin (73 μL, 64 mg, 0.5 mmol) with a reaction time of 48 h. The ratio of the two isomers in the crude reaction mixture by GC was 95:5. Kugelrohr distillation furnished a mixture of the two isomeric borylated products (112 mg, 73%) as a white solid. The ratio of the two isomers in the isolated product by GC was 97:3. gHMBC spectroscopy (FIG. 2) was used to assign the major isomer as 4-bromo-2-(4,4,5,5-tetramethyl-1,3,2-dioxaboryl)benzonitrile. $^1$H NMR (CDCl$_3$, 500 MHz): δ (major isomer) 7.97 (d, J=2.0 Hz, 1H, H$_a$), 7.62 (dd, J=8.3, 2.0 Hz, 1H, H$_b$), 7.50 (d, J=8.3 Hz, 1H, H$_c$), 1.33 (br s, 12H); $^{13}$C NMR {$^1$H} (CDCl$_3$, 125 MHz): δ (major isomer) 138.8 (C2), 134.5 (C5), 134.2 (C6), 127.1 (C1), 118.1 (nitrile C7), 115.8 (C4), 85.0 (C8), 24.7 (C9); $^{11}$B NMR (CDCl$_3$, 96 MHz): δ 29.92; FT-IR (neat): 2980, 2228, 1582, 1551, 1480, 1416, 1399, 1373, 1335, 1271, 1144, 1084, 1069, 963, 862, 841, 763, 673 cm$^{-1}$; LRMS (% rel. int.): m/e (major isomer) 307 M⁺ (16), 292 (51), 266 (100), 251 (45), 228 (17), 170 (15); Anal. Calcd for $C_{13}H_{15}BBrNO_2$: C, 50.70; H, 4.91; N, 4.55. Found: C, 50.29; H, 4.75; N, 4.57. HRMS Calcd for $C_{13}H_{15}BBrNO_2$: 307.0379. Found: 307.0376.

EXAMPLE 4

Borylation of 4-Iodobenzonitrile

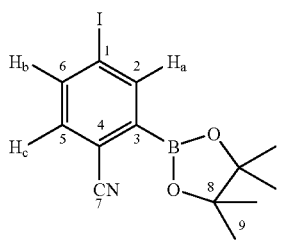

General procedure B was applied to 4-iodobenzonitrile (229.1 mg, 1 mmol, 1 equivalent) and B$_2$Pin$_2$ (254.0 mg, 1 mmol, 2 equivalents of boron) with a reaction time of 40 h. Only one isomer was observed in crude reaction mixture by GC and by $^1$H NMR spectroscopy. Solvent was removed under reduced pressure, and the crude mixture was eluted with CH$_2$Cl$_2$ through a plug of silica gel to afford the single pure isomer (255 mg, 71%) as a white solid, mp 77-79° C. gHMBC spectroscopy (FIG. 3) was used to assign the single isomer as 4-iodo-2-(4,4,5,5-tetramethyl-1,3,2-dioxaboryl) benzonitrile. $^1$H NMR (CDCl$_3$, 500 MHz): δ 8.19 (d, J=2.0 Hz, 1H, H$_a$), 7.85 (dd, J=8.3, 2.0 Hz, 1H, H$_b$), 7.36 (d, J=8.3 Hz, 1H, H$_c$), 1.34 (br s, 12H); $^{13}$C NMR {$^1$H} (CDCl$_3$, 125 MHz): δ 144.6 (C2), 140.1 (C6), 134.3 (C5), 118.3 (nitrile C7), 116.3 (C4), 99.8 (C1), 85.1 (C8), 24.7 (C9); $^{11}$B NMR (CDCl$_3$, 96 MHz): δ 29.77; FT-IR (neat): 2980, 2228, 1576, 1545, 1480, 1414, 1395, 1374, 1335, 1271, 1140, 1071, 963, 859, 839, 826, 673 cm$^{-1}$; LRMS (% rel. int.): m/e 355 M⁺ (42), 340 (75), 314 (100), 297 (72), 256 (77), 228 (11); Anal. Calcd for $C_{13}H_{15}BINO_2$: C, 43.99; H, 4.26; N, 3.95. Found: C, 44.17; H, 4.44; N, 3.88.

EXAMPLE 5

Borylation of 4-methylbenzonitrile

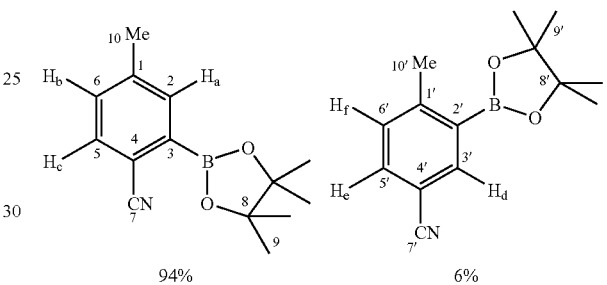

94%    6%

General procedure A was applied to 4-methylbenzonitrile (468.6 mg, 4 mmol) and HBPin (145 μL, 128 mg, 1 mmol) using 6 mol % [Ir] with a reaction time of 72 h. The ratio of the two isomers in the crude reaction mixture by GC was 94:6. Kugelrohr distillation furnished a mixture of the two isomeric borylated products (156 mg, 64%) as colorless oil which solidified on standing. The ratio of the two isomers in the isolated product by GC was 92:8. The major isomer was assigned as 4-methyl-2-(4,4,5,5-tetramethyl-1,3,2-dioxaboryl)benzonitrile by the NOESY1D spectrum and by preparing an authentic sample using a slightly modified literature procedure (Miyaura, N., et al., Tetrahedron 2001, 57, 9813-9816). $^1$H NMR (CDCl$_3$, 500 MHz): δ (major isomer) 7.67 (br s, 1H, H$_a$), 7.57 (d, J=7.9 Hz, 1H, H$_b$ or H$_c$), 7.30 (d, J=7.9 Hz, 1H, H$_b$ or H$_c$), 2.38(s, 3H), 1.36 (br s, 12H); $^{13}$C NMR {$^1$H} (CDCl$_3$, 125 MHz): δ (major isomer) 142.2 (C1), 136.5, 133.4, 131.8 (C2, C5 and C6), 119.2 (nitrile C7), 114.2 (C4), 84.7 (C8), 24.8 (C9), 21.5 (C10); $^{11}$B NMR (CDCl$_3$, 96 MHz): δ 30.36; FT-IR (neat): 2980, 2932, 2226, 1603, 1491, 1447, 1408, 1391, 1381, 1373, 1346, 1265, 1213, 1140, 1069, 965, 853, 828, 675, 661 cm$^{-1}$; LRMS (% rel. int.): m/e 243 M⁺ (46), 228 (70), 202 (100), 185 (52), 144 (92), 117 (25); Anal. Calcd for $C_{14}H_{18}BNO_2$: C, 69.17; H, 7.46; N, 5.76. Found: C, 68.74; H, 7.64; N, 5.62. HRMS Calcd for $C_{14}H_{18}BNO_2$: 243.1431. Found: 243.1425.

Preparation of an Authentic Sample of 4-methyl-2-(4,4,5,5-tetramethyl-1,3,2-dioxaboryl)-benzonitrile In a glove box, a 100 mL schlenk flask, equipped with a magnetic stirring bar, was charged with Pd$_2$(dba)$_3$ (13.8 mg, 0.015 mmol, 3 mol % Pd) and tricyclohexylphosphine (PCy$_3$, 20.2 mg, 0.072 mmol, 7.2 mol %). Dioxane (6 mL) was added and the resulting mixture was stirred for 30 minutes at room temperature. B₂Pin₂ (280 mg, 1.1 mmol), KOAc (147 mg, 1.5 mmol), and 2-bromo-4-methylbenzonitrile (196 mg, 1 mmol) were added successively. The schlenk flask was brought to a schlenk line. A condenser was attached, and the flask was flushed with nitrogen. The reaction mixture was stirred at 80° C. for 12 h. The mixture was treated with water (5 mL), and the product was extracted with ether, washed with brine, and dried over MgSO₄. Kugelrohr distillation furnished the desired product (151 mg, 62%) as a colorless oil. Its spectral data matched the major isomer obtained from the catalytic borylation of 4-methylbenzonitrile described earlier.

EXAMPLE 6

Borylation of 4-methoxylbenzonitrile

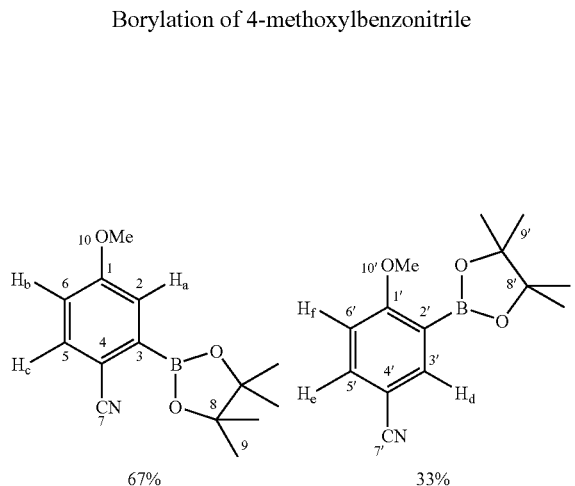

67%    33%

General procedure A was applied to 4-methoxybenzonitrile (266.3 mg, 2 mmol) and HBPin (73 µL, 64 mg, 0.5 mmol) with a reaction time of 24 h. The ratio of the two isomers in the crude reaction mixture by $^1$H NMR spectroscopy was 67:33. Kugelrohr distillation furnished a mixture of the two isomeric borylated products (84 mg, 65%) as a colorless oil. The ratio of the two isomers in the isolated product by $^1$H NMR spectroscopy was 67:33. The NOESY1D and gHMBC spectra (FIG. 4) were used to assign the major isomer as 4-methoxy-2-(4,4,5,5-tetramethyl-1,3,2-dioxaboryl)benzonitrile. $^1$H NMR (CDCl₃, 500 MHz): δ (major isomer) 7.59 (d, J=8.5 Hz, 1H, H$_c$), 7.31 (d, J=2.9 Hz, 1H, H$_d$), 6.97 (dd, J=8.5, 2.9 Hz, 1H, H$_b$), 3.84 (s, 3H), 1.35 (br s, 12H), (minor isomer) 7.93 (d, J=2.4 Hz, 1H, H$_d$), 7.65 (dd, J=8.8, 2.4 Hz, 1H, H$_e$), 6.87 (d, J=8.8 Hz, 1H, H$_f$), 3.85 (s, 3H), 1.32 (br s, 12H); $^{13}$C NMR {$^1$H} (CDCl₃, 125 MHz): δ (major isomer) 161.7 (C1), 135.3 (C5), 120.6 (C2), 119.3 (nitrile C7), 117.0 (C6), 108.8 (C4), 84.8 (C8), 55.5 (C10), 24.73 (C9), (minor isomer) 166.9 (C1'), 140.9 (C3'), 136.6 (C5'), 119.2 (nitrile C7'), 110.7 (C6'), 103.6 (C4'), 84.1 (C8'), 55.5 (C10'), 24.7 (C9'); $^{11}$B NMR (CDCl₃, 96 MHz): δ 30.50; FT-IR (neat): 2980, 2942, 2842, 2224, 1601, 1493, 1466, 1449, 1424, 1412, 1373, 1345, 1271, 1238, 1144, 1060, 1030, 965, 853, 830 cm⁻¹; LRMS (% rel. int.): m/e 259 M⁺ (100), 244 (61), 232 (9), 216 (73), 201 (65), 186 (25), 174 (20), 160 (79); HRMS Calcd for C₁₄H₁₈BNO₃: 259.1380. Found: 259.1383.

EXAMPLE 7

Borylation of 4-thiometylbenzonitrile

90%    10%

General procedure A was applied to 4-thiomethylbenzonitrile (298.5 mg, 2 mmol, 2 equivalents) and B₂Pin₂ (127 mg, 0.5 mmol, 1 equivalent of boron) at 80° C. with a reaction time of 18 h. The ratio of the two isomers in the crude reaction mixture by $^1$H NMR spectroscopy was 90:10. Kugelrohr distillation gave a fraction (155 mg) containing two isomers along with small amount of d$^t$bpy. Passing a CH₂Cl₂ solution of that fraction through a plug of silica furnished a mixture of two isomeric borylated products (150 mg, 55%) as a white solid. The ratio of the two isomers in the isolated product by $^1$H NMR spectroscopy was 87:13. The NOESY1D and gHMBC spectra (FIG. 5) were used to assign the major isomer as 4-thiomethyl-2-(4,4,5,5-tetramethyl-1,3,2-dioxaboryl)benzonitrile. $^1$H NMR (CDCl₃, 500 MHz): δ (major isomer) 7.63 (d, J=2.0 Hz, 1H, H$_d$), 7.54 (d, J=8.3 Hz, 1H, H$_c$), 7.27 (dd, J=8.3, 2.0 Hz, 1H, H$_b$), 2.48 (s, 3H), 1.35 (br s, 12H), (minor isomer) 7.92 (d, J=2.0 Hz, 1H, H$_d$), 7.56 (dd, J=8.3, 2.0 Hz, 1H, H$_e$), 7.14 (d, J=8.3 Hz, 1H, H$_f$), 2.44 (s, 3H), 1.34 (br s, 12H); $^{13}$C NMR {$^1$H} (CDCl₃, 125 MHz): δ (major isomer) 144.7 (C1), 133.4 (C5), 132.2 (C2), 127.1 (C6), 119.1 (nitrile C7), 112.4 (C4), 84.8 (C8), 24.7 (C9), 14.61 (C10), (minor isomer) 152.7 (C1'), 139.3 (C3'), 134.1 (C5'), 122.9 (C6'), 119.0 (nitrile C7'), 106.7 (C4'), 84.6 (C8'), 24.7 (C9'), 15.0 (C10'); $^{11}$B NMR (CDCl₃, 96 MHz): δ 30.27; FT-IR (neat): 2980, 2928, 2224, 1584, 1547, 1483, 1397, 1381, 1373, 1345, 1269, 1213, 1167, 1142, 1107, 1059, 963, 871, 847, 825, 769, 741, 669 cm⁻¹; LRMS (% rel. int.): m/e 275 M⁺ (100), 260 (26), 232 (41), 217 (46), 202 (9), 190 (10), 175 (54); Anal. Calcd for C₁₄H₁₈BNO₂S: C, 61.11; H, 6.59; N, 5.09. Found: C, 61.24; H, 6.95; N, 5.05; HRMS Calcd for $C_{14}H_{18}BNO_2S$: 275.1151. Found: 275.1157.

EXAMPLE 8

Borylation of 4-dimethylaminobenzonitrile

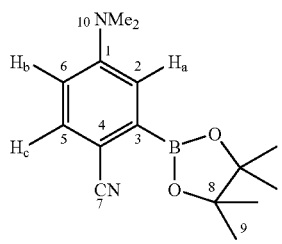

General procedure B was applied to 4-dimethylaminobenzonitrile (146.2 mg, 1 mmol, 1 equivalent) and $B_2Pin_2$ (254.0 mg, 1 mmol, 2 equivalents of boron) using 6 mol % [Ir] with a reaction time of 72 h. Only one isomer was observed in the crude reaction mixture by GC and by $^1$H NMR spectroscopy. Solvent was removed under reduced pressure, and the crude mixture was eluted with $CH_2Cl_2$ through a plug of silica gel to afford the single pure isomer (180 mg, 66%) as a white solid, mp 110-111° C. The NOESY1D and gHMBC spectra (FIG. 6) were used to assign the single isomer as 4-dimethylamino-2-(4,4,5,5-tetramethyl-1,3,2-dioxaboryl)benzonitrile. $^1$H NMR (CDCl$_3$, 300 MHz): δ 7.48 (d, J=8.8 Hz, 1H, H$_c$), 7.04 (d, J=2.9 Hz, 1H, H$_a$), 6.67 (dd, J=8.8, 2.9 Hz, 1H, H$_b$), 3.01(s, 6H), 1.35 (br s, 12H); $^{13}$C NMR {$^1$H} (CDCl$_3$, 75 MHz): δ 151.4 (C1), 134.8 (C5), 120.7 (nitrile C7), 118.1 (C2), 113.2 (C6), 102.3 (C4), 84.5 (C8), 39.9 (C10), 24.7 (C9); $^{11}$B NMR (CDCl$_3$, 96 MHz): δ 30.5; FT-IR (neat): 2980, 2932, 2815, 2213, 1597, 1553, 1508, 1485, 1429, 1416, 1374, 1337, 1271, 1230, 1169, 1144, 1053, 968, 847, 816 cm$^{-1}$; LRMS (% rel. int.): m/e 272 M$^+$ (100), 257 (7), 229 (11), 214 (11), 189 (6), 173 (23); Anal. Calcd for $C_{15}H_{21}BN_2O_2$: C, 66.2; H, 7.78; N, 10.29. Found: C, 66.54; H, 7.76; N, 10.06.

EXAMPLE 9

Borylation of methyl 4-cyanobenzoate

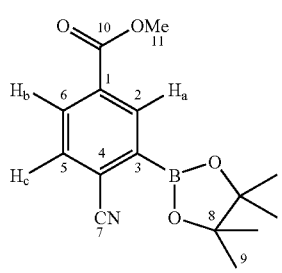

General procedure B was applied to methyl 4-cyanobenzoate (161.2 mg, 1 mmol, 1 equivalent) and $B_2Pin_2$ (203.0 mg, 0.8 mmol, 1.6 equivalents of boron) with a reaction time of 48 h. Only one isomer was observed in the crude reaction mixture by GC and by $^1$H NMR spectroscopy. Solvent was removed under reduced pressure, and the crude mixture was eluted with $CH_2Cl_2$ through a plug of silica gel to afford the single pure isomer (190 mg, 66%) as a white solid, mp 136-137° C. The NOESY1D and gHMBC spectra (FIG. 7) were used to assign the single isomer as methyl 4-cyano-3-(4,4,5,5-tetramethyl-1,3,2-dioxaboryl)benzoate. $^1$H NMR (CDCl$_3$, 300 MHz): δ 8.49 (d, J=1.7 Hz, 1H, H$_a$), 8.14 (dd, J=8.1, 1.9 Hz, 1H, H$_b$), 7.75 (d, J=8.1 Hz, 1H, H$_c$), 3.93 (s, 3H), 1.37 (br s, 12H); $^{13}$C NMR {$^1$H} (CDCl$_3$, 75 MHz): δ 165.6 (C10), 136.6 (C2), 133.4 (C5), 132.7 (C1), 131.9 (C6), 121.1 (C4), 118.1 (nitrile C7), 85.1 (C8), 52.6 (C11), 24.8 (C9); $^{11}$B NMR (CDCl$_3$, 96 MHz): δ 30.1; FT-IR (neat): 2980, 2954, 2230, 1721, 1603, 1487, 1410, 1375, 1337, 1279, 1251, 1144, 1115, 1069, 976, 851, 770, 654 cm$^{-1}$; LRMS (% rel. int.): m/e 287 M$^+$ (5), 272 (32), 256 (20), 244 (100), 229 (18), 188 (26), 156 (14); Anal. Calcd for $C_{15}H_{18}BNO_4$: C, 62.75; H, 6.32; N, 4.88. Found: C, 62.33; H, 6.26; N, 4.79. HRMS Calcd for $C_{15}H_{18}BNO_4$: 287.1329. Found: 287.1327.

EXAMPLE 10

Borylation of 4'-cyanoacetanilide

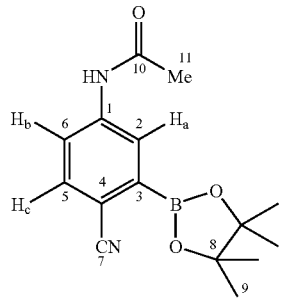

General procedure B was applied to 4'-cyanoacetanilide (160.2 mg, 1 mmol, 1 equivalent) and $B_2Pin_2$ (406 mg, 1.6 mmol, 3.2 equivalents of boron) using 8 mol % [Ir] with a reaction time of 18 h. One borylated isomer was observed in the crude reaction mixture by GC and by $^1$H NMR spectroscopy along with a small amount of borylated/reduced (reduction of carbonyl group to $CH_2$) as a side product. Solvent was removed under reduced pressure. Column chromatography (ether, Rf=0.5) gave a mixture of the desired product and pinacol (239 mg). Kugelrohr distillation furnished the desired product (177 mg, 62%) as a white solid, mp 178-180° C. The gHMBC spectrum (FIG. 8) was used to assign the single isomer as 4'-cyano-3'-(4,4,5,5-tetramethyl-1,3,2-dioxaboryl)acetanilide. $^1$H NMR (CDCl$_3$, 500 MHz): δ 7.99 (dd, J=8.3, 2.0 Hz, 1H, H$_b$), 7.85 (s, 1H, N—H), 7.77 (d, J=2.4 Hz, 1H, H$_a$), 7.63 (d, J=8.3 Hz, 1H, H$_c$), 2.18 (s, 3H), 1.32 (br s, 12H); $^{13}$C NMR {$^1$H} (CDCl$_3$, 75 MHz): δ 168.8 (C10), 141.1 (C1), 134.7 (C5), 125.9 (C2), 121.5 (C6), 119 (nitrile C7), 111.6 (C4), 84.8 (C8), 24.7 (C9), 24.6 (C11); $^{11}$B NMR (CDCl$_3$, 96 MHz): δ 30.52; FT-IR (neat): 3319, 3104, 2980, 2934, 2225, 1701, 1678, 1601, 1578, 1532, 1497, 1416, 1373, 1344, 1302, 1258, 1140, 1063, 965, 853, 800, 743, 675 cm$^{-1}$; LRMS (% rel. int.): m/e 286 M$^+$ (100), 271 (18), 253 (32), 244 (89), 228

(68), 201 (42), 187 (68), 158 (13), 144 (58); HRMS Calcd for $C_{15}H_{19}BN_2O_3$: 286.1489. Found: 286.1493.

EXAMPLE 11

Borylation of 4-(trifluoromethyl)benzonitrile

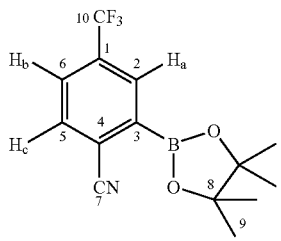

General procedure B was applied to 4-(trifluoromethyl) benzonitrile (171.1 mg, 1 mmol, 1 equivalent) and HBPin (175 μL, 154 mg, 1.2 mmol) in n-hexane (3 mL) with a reaction time of 12 h. One monoborylated product and one diborylated product were observed in the crude reaction mixture by GC (90:10). Solvent was removed under reduced pressure. The crude mixture was eluted with $CH_2Cl_2$ through a plug of silica gel. Sublimation furnished the desired single monoborylated product (203 mg, 68%) as a white solid, mp 79-80° C. $^{13}C$ NMR spectroscopy was used to assign the single isomer as 4-(trifluoromethyl)-2-(4,4,5,5-tetramethyl-1,3,2-dioxaboryl)benzonitrile. $^1H$ NMR (CDCl$_3$, 500 MHz): δ 8.12 (s, 1H, H$_a$), 7.81 (d, J=7.8 Hz, 1H, H$_b$ or H$_c$), 7.76 (d, J=7.8 Hz, 1H, H$_b$ or H$_c$), 1.38 (br s, 12H); $^{13}C$ NMR {$^1H$} (CDCl$_3$, 125 MHz): δ 133.7 (C5), 133.3 (q, $^2J_{C-F}$=33.2 Hz, C1), 132.5 (q, $^3J_{C-F}$=2.1 Hz, C2), 127.8 (q, $^3J_{C-F}$=3.3 Hz, C6), 122.1 (q, $^1J_{C-F}$=273 Hz, C10), 120.7 (C4), 117.6 (nitrile C7), 85.3 (C8), 24.7 (C9); $^{11}B$ NMR (CDCl$_3$, 96 MHz): δ 30.03; $^{19}F$ NMR (CDCl$_3$, 282 MHz): δ −63.4; FT-IR (neat): 2982, 2234, 1613, 1574, 1423, 1354, 1306, 1271, 1175, 1142, 1082, 1065, 965, 878, 849, 675 cm$^{-1}$; LRMS (% rel. int.): m/e 297 M$^+$ (23), 282 (100), 256 (81), 239 (27), 198 (19), 171 (10); HRMS Calcd for $C_{14}H_{15}BF_3NO_2$: 297.1148. Found: 297.1144.

EXAMPLE 12

Borylation of Benzonitrile

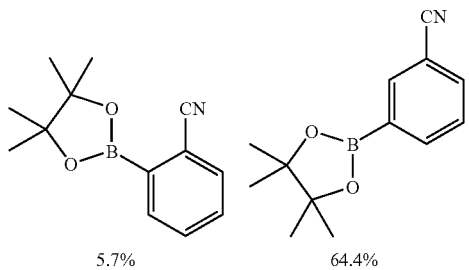

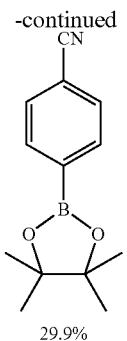

General procedure A was applied to benzonitrile (412.5 mg, 4 mmol) and HBPin (145 μL, 128 mg, 1 mmol) with a reaction time of 12 h. The ratio of the three isomers in the crude reaction mixture by GC was 5.7:64.4:29.9. Solvent and excess substrate were removed under reduced pressure. The crude mixture was eluted with $CH_2Cl_2$ through a plug of silica gel to afford a mixture of the three isomeric borylated products (176 mg, 77%) as a white solid. $^1H$ NMR, gCOSY, and gHMBC spectroscopy were used to assign the major isomer as 3-(4,4,5,5-tetramethyl-1,3,2-dioxaboryl)benzonitrile. $^1H$ NMR (CDCl$_3$, 300 MHz): δ (major/meta isomer) 8.07-8.05 (br s, 1H), 7.98 (td, J=7.5, 1.2 Hz, 1H), 7.71-7.67 (m, 1H), 7.44 (dt, J=7.5, 0.7 Hz, 1H), 1.32 (br s, 12H), (minor/para isomer) 7.87-7.84 (m, 2H), 7.62-7.59 (m, 2H), 1.32 (br s, 12H); $^{13}C$ NMR {$^1H$} (CDCl$_3$, 75 MHz): δ (major/meta isomer) 138.7, 138.3, 134.3, 128.3, 118.7, 112, 84.4, 24.8, (minor/para isomer) 135, 131, 118.7, 114.4, 84.7, 24.8; $^{11}B$ NMR (CDCl$_3$, 96 MHz): δ 31.2; FT-IR (neat): 3063, 2980, 2934, 2230, 1603, 1483, 1398, 1360, 1329, 1271, 1143, 1088, 964, 880, 849, 700, 653 cm$^{-1}$; LRMS (% rel. int.): m/e (major/meta isomer) 229 M$^+$ (11), 230 M$^{+1}$ (29), 214 (100), 186 (10), 143 (44), (minor/para isomer) 229 M$^+$ (5), 230 M$^{+1}$ (14), 186 (9), 143 (41); HRMS Calcd for $C_{13}H_{16}BNO_2$: 229.1274. Found: 229.1271.

EXAMPLE 13

Borylation of 2-fluoro-4-bromobenzonitrile

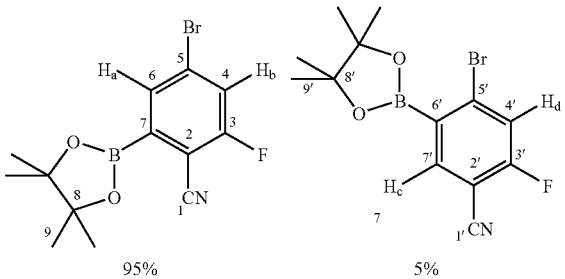

General procedure B was applied to 2-fluoro-4-bromobenzonitrile (200 mg, 1 mmol, 1 equivalent) and HBPin (290 μL, 256 mg, 2 mmol, 2 equivalent) with a reaction time of 9 h. The ratio of the two borylated isomers in the crude reaction mixture by $^1H$ NMR spectroscopy was 95:5. A small amount of diborylated product was also observed. Solvent was removed under reduced pressure, and the crude mixture was eluted with $CH_2Cl_2$ through a plug of silica gel. Sublimation afforded a mixture of two isomeric borylated products (278 mg, 85%) as a white solid. The ratio of the two borylated isomers in the isolated product by $^1$H NMR spectroscopy was 95:5. $^1$H NMR spectroscopy were used to assign the major isomer as 2-fluoro-4-bromo-6-(4,4,5,5-tetramethyl-1,3,2-dioxaboryl)-benzonitrile. $^1$H NMR (CDCl$_3$, 500 MHz): δ (major isomer) 7.77 (d, J=1.7 Hz, 1H), 7.44 (dd, $^2$J$_{H-F}$=8.3 Hz, J=1.7 Hz, 1H), 1.35 (br s, 12H), (minor isomer) 7.90 (d, $^3$J$_{H-F}$=7.5 Hz, 1H), 7.42 (d, $^2$J$_{H-F}$=8.5 Hz, 1H), 1.35 (br s, 12H); $^{13}$C NMR {$^1$H} (CDCl$_3$, 75 MHz): δ (major isomer) 163.3 (d, $^1$J$_{C-F}$=262.8 Hz, C3), 134.6 (d, $^4$J$_{C-F}$=4 Hz, C6), 127.8 (d, $^3$J$_{C-F}$=8 Hz, C5), 122 (d, $^2$J$_{C-F}$=23 Hz, C4), 112.9 (nitrile, C1), 104.6 (d, $^2$J$_{C-F}$=14.1 Hz, C2), 85.4, 24.7; $^{11}$B NMR (CDCl$_3$, 96 MHz): δ 29.94; $^{19}$F NMR (CDCl$_3$, 282 MHz): δ (major isomer) −103.9 (d, J=7.9 Hz); FT-IR (neat): 3086, 2986, 2934, 2237, 1590, 1557, 1462, 1408, 1375, 1358, 1329, 1140, 972, 985, 880, 843, 742, 665 cm$^{-1}$; LRMS (% rel. int.): m/e (major isomer) 325 M$^+$ (15), 310 (37), 284 (67), 267 (34), 246 (31), 226 (57); Anal. Calcd for C$_{13}$H$_{14}$BBrFNO$_2$: C, 47.90; H, 4.33; N, 4.3. Found: C, 48.15, H, 4.28; N, 4.16.

EXAMPLE 14

Borylation of 3,4-dichlorobenzonitrile

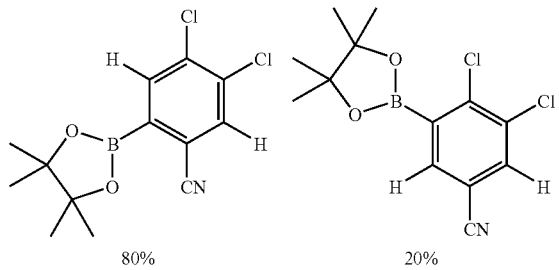

80%  20%

General procedure B was applied to 3,4-dichlorobenzonitrile (172 mg, 1 mmol, 1 equivalent) and HBPin (218μL, 192 mg, 1.5 mmol, 1.5 equivalent) with a reaction time of 18 h. The ratio of the two borylated isomers in the crude reaction mixture by $^1$H NMR spectroscopy was 80:20. Solvent was removed under reduced pressure and the crude mixture was eluted with CH$_2$Cl$_2$ through a plug of silica gel to afford a mixture of two isomeric borylated products (265 mg, 89%) as a white solid. The ratio of the two borylated isomers in the isolated product by $^1$H NMR spectroscopy was 81:19. $^1$H NMR spectroscopy was used to assign the major isomer as 4,5-dichloro-2-(4,4,5,5-tetramethyl-1,3,2-dioxaboryl)-benzonitrile. $^1$H NMR (CDCl$_3$, 500 MHz): δ (major isomer) 7.92 (s, 1H), 7.73 (s, 1H), 1.35 (br s, 12H), (minor isomer) 7.84 (d, J=2 Hz, 1H), 7.74 (d, J=2 Hz, 1H), 1.35 (br s, 12H); $^{13}$C NMR {$^1$H} (CDCl$_3$, 125 MHz): δ (major isomer) 137.7, 137.1, 135.8, 134.8, 116.9, 111.3, 85.3, 24.7, (minor isomer) 142.7, 137.6, 135, 134.3, 116.8, 111.3, 85, 24.7; $^{11}$B NMR (CDCl$_3$, 96 MHz): δ 29.9; FT-IR (neat): 2982, 2234, 1580, 1535, 1472, 1383, 1342, 1304, 1142, 1084, 964, 910, 850, 669 cm$^{-1}$; LRMS (% rel. int.): m/e (major isomer) 297 M$^+$ (22), 282 (60), 256 (100), 239 (48), 198 (41), (minor isomer) 297 M$^+$ (1), 282 (28), 262 (100), 220 (80); Anal. Calcd for C$_{13}$H$_{14}$BCl$_2$NO$_2$: C, 52.40; H, 4.74; N, 4.70. Found: C, 52.42; H, 4.79; N, 4.55; HRMS Calcd for C$_{13}$H$_{14}$BCl$_2$NO$_2$: 297.0495. Found: 297.0500.

EXAMPLE 15

Diborylation of 4-fluorobenzonitrile

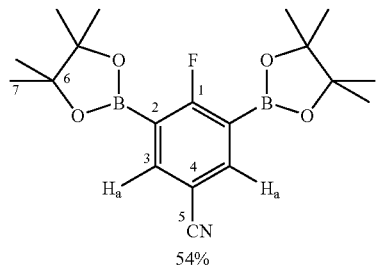

54%

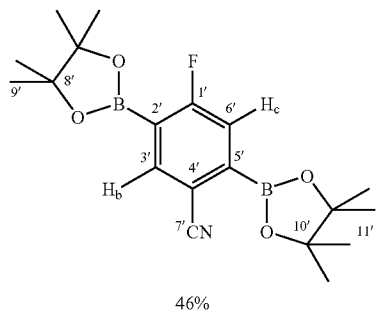

46%

General procedure C was applied to 4-fluorobenzonitrile (121.2 mg, 1 mmol, 1 equivalent) and HBPin (580 μL, 512 mg, 4 mmol, 4 equivalent) with a reaction time of 24 h. The ratio of the two isomers in the crude reaction mixture by $^1$H NMR spectroscopy was 54:46. Solvent was removed under reduced pressure, and the crude mixture was eluted with CH$_2$Cl$_2$ through a plug of silica gel to afford a mixture of two isomeric diborylated products (343 mg, 92%) as a white solid. The ratio of the two diborylated isomers in the isolated product by $^1$H NMR spectroscopy was 53:47. $^1$H, $^{13}$C NMR and gHMBC spectroscopy were used to assign the major isomer as 4-fuoro-3,5-bis-(4,4,5,5-tetramethyl-1,3,2-dioxaboryl)-benzonitrile. $^1$H NMR (CDCl$_3$, 500 MHz): δ (major isomer) 8.1 (d, $^4$J$_{H-F}$=4.9 Hz, 2H, H$_a$), 1.28 (br s, 24H), (minor isomer) 8.04 (d, $^4$J$_{H-F}$=5.4 Hz, 1H, H$_b$), 7.46 (d, $^3$J$_{H-F}$=8.8 Hz, 1H, H$_c$), 1.32 (s, 12H), 1.31 (s, 12H); $^{13}$C NMR {$^1$H} (CDCl$_3$, 125 MHz): δ (major isomer) 172 (d, $^1$J$_{C-F}$=266 Hz, C1), 143.9 (d, $^3$J$_{C-F}$=10.9 Hz, C3), 117.9 (nitrile C5), 108 (d, $^4$J$_{C-F}$=3.6 Hz, C4), 84.4 (C6), 24.7(C7), (minor isomer) 168.1 (d, $^1$J$_{C-F}$=261.4 Hz, C1'), 142.6 (d, $^3$J$_{C-F}$=8.8 Hz, C3'), 122.6 (d, $^2$J$_{C-F}$=23.8 Hz, C6'), 118.1 (nitrile C7'), 112.6 (d, $^4$J$_{C-F}$=3.6 Hz, C4'), 85, 84.5, 24.7; $^{11}$B NMR (CDCl$_3$, 96 MHz): δ 29.8; $^{19}$F NMR (CDCl$_3$, 282 MHz): δ (major isomer) −81.8 (m), (minor isomer) −94.9 (m); FT-IR (neat): 2980, 2934, 2232, 1599, 1497, 1437, 1414, 1373, 1334, 1267, 1215, 1142, 1095, 966, 889, 848, 584 cm$^{-1}$; LRMS (% rel. int.): m/e (major isomer) 373 M$^+$ (4), 358 (59), 353 (100), 315 (22), 253 (45), (minor isomer) 373 M$^+$ (32), 358 (68), 331 (100), 315

EXAMPLE 16

Diborylation of 4-methoxybenzonitrile

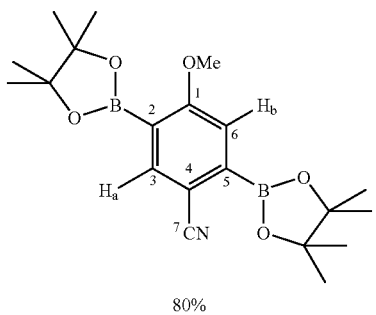

80%

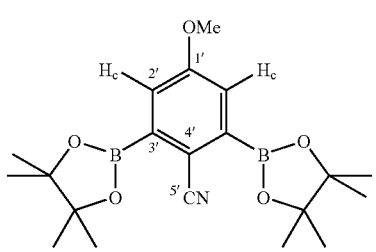

20%

General procedure C was applied to 4-methoxybenzonitrile (133.2 mg, 1 mmol, 1 equivalent) and HBPin (580 μL, 512 mg, 4 mmol, 4 equivalent) at 60° C. for 48 h. The ratio of the two diborylated isomers in the crude reaction mixture by $^1$H NMR spectroscopy was 80:20. Solvent was removed under reduced pressure, and the crude mixture was eluted with CH$_2$Cl$_2$ through a plug of silica gel to afford a mixture of two isomeric diborylated products (310 mg, 81%) as a white solid. The ratio of the two diborylated isomers in the isolated product by $^1$H NMR spectroscopy was 80:20. $^1$H NMR and gHMBC spectroscopy were used to assign the major isomer as 4-methoxy-2,5-bis-(4,4,5,5-tetramethyl-1,3,2-dioxaboryl)-benzonitrile. $^1$H NMR (C$_6$D$_6$, 500 MHz): δ (major isomer) 8.42 (s, 1H, H$_a$), 7.36 (s, 1H, H$_b$), 3.20 (s, 3H), 1.10 (br s, 12H), 1.06 (br s, 12H), (minor isomer) 7.61 (s, 2H, H$_c$), 3.08 (s, 3H), 1.11 (br s, 12H); $^{13}$C NMR {$^1$H} (C$_6$D$_6$, 125 MHz): δ (major isomer) 166.3 (C1), 143.1 (C3), 137.4 (br, C5), 122.1 (br, C2), 119.32 (nitrile, C7), 117.36 (C6), 110.1 (C4), 84.8, 83.8, 24.79, 24.76, (minor isomer) 160.8 (C1'), 123.4 (C2'), 118.6 (nitrile C5'), 114.9 (C4'), 84.6 24.8; $^{11}$B NMR (CDCl$_3$, 96 MHz): δ 30.90; FT-IR (neat): 2980, 2936, 2224, 1601, 1503, 1398, 1373, 1337, 1244, 1142, 1094, 964, 858 cm$^{-1}$; LRMS (% rel. int.): m/e 385 M$^+$ (100), 370 (63), 343 (53), 274 (39); Anal. Calcd for C$_{19}$H$_{26}$B$_2$FNO$_4$: C, 61.17; H, 7.03; N, 3.75. Found: C, 61.37,; H, 6.83; N, 3.82.

EXAMPLE 17

Diborylation of 4-chlorobenzonitrile

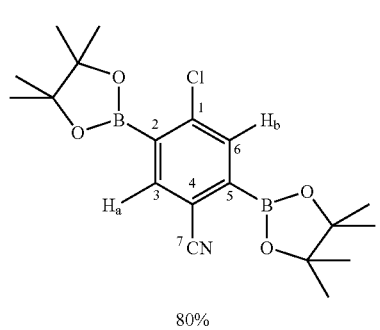

80%

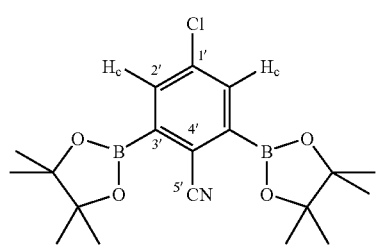

20%

General procedure C was applied to 4-chlorobenzonitrile (137.6 mg, 1 mmol, 1 equivalent) and HBPin (580 μL, 512 mg, 4 mmol, 4 equivalent) with a reaction time of 48 h. The ratio of the two diborylated isomers in the crude reaction mixture by GC-FID was 80:20. Solvent was removed under reduced pressure, and the crude mixture was eluted with CH$_2$Cl$_2$ through a plug of silica gel to afford a mixture of two isomeric diborylated products (320 mg, 82%) as a white solid. The ratio of the two diborylated isomers in the isolated product by GC-FID was 80:20. $^1$H NMR and gHMBC spectroscopy were used to assign the major isomer as 4-chloro-2,5-bis-(4,4,5,5-tetramethyl-1,3,2-dioxaboryl)-benzonitrile.
$^1$H NMR (CDCl$_3$, 500 MHz): δ (major isomer) 7.97 (s, 1H, H$_a$), 7.80 (s, 1H, H$_b$), 1.35 (br s, 12H), 1.344 (br s, 12H), (minor isomer) 7.83 (s, 2H, H$_c$), 1.349 (br s, 12H); $^{13}$C NMR {$^1$H} (CDCl$_3$, 125 MHz): δ (major isomer) 143.6 (C1), 141.2 (C3), 136.5 (C6), 118.2 (nitrile, C7), 114.8 (C4), 85.1, 84.8, 24.7, (minor isomer) 137.7 (C1'), 137.3 (C2'), 119.7(C4'), 117.6 (nitrile C5'), 85.04,24.7; $^{11}$B NMR (CDCl$_3$, 96 MHz): δ 30.25; FT-IR (neat): 2980, 2230, 1591, 1383, 1341, 1269, 1142, 1122, 1088, 962, 855 cm$^{-1}$; LRMS (% rel. int.): m/e (major isomer) 389 M$^+$ (30), 374 (57), 354 (100), 347 (88), 331 (39), 312 (37), 290 (35), (minor isomer) 389 M$^+$ (36), 374 (64), 348 (23),290 (53), 248 (49), 207 (100); Anal. Calcd for C$_{20}$H$_{29}$B$_2$NO$_5$: C, 62.38; H, 7.59; N, 3.64. Found: C, 62.36; H, 7.41; N, 3.69.

$C_{19}H_{26}B_2ClNO_4$: C, 58.59; H, 6.73; N, 3.6. Found: C, 58.27, H, 6.78; N, 3.41; HRMS Calcd for $C_{19}H_{26}B_2ClNO_4$: 389.1736. Found: 389.1746.

EXAMPLE 18

Diborylation of 1,4-dicyanobenzene

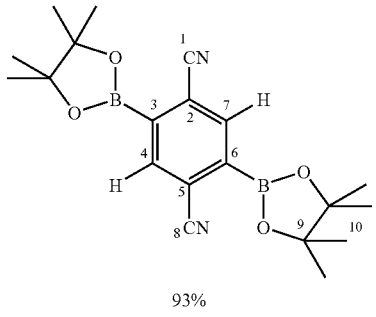

93%

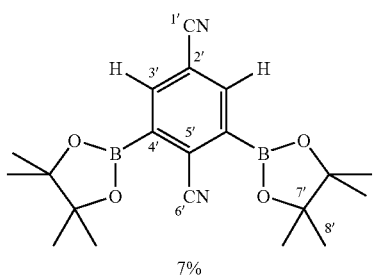

7%

General procedure C was applied to 1,4-dicyanobenzene (128.2 mg, 1 mmol, 1 equivalent) and HBPin (580 μL, 512 mg, 4 mmol, 4 equivalent) with a reaction time of 20 h. The ratio of the two diborylated isomers in the crude reaction mixture by GC-FID was 93:7. Solvent was removed under reduced pressure. Crystallization from THF/pentane gave the major isomer (270 mg, 71%) as a white solid, mp 242-245° C. $^{13}$C NMR spectroscopy were used to assign the major isomer as 2,5-bis-(4,4,5,5-tetramethyl-1,3,2-dioxaboryl)-1,4-dicyanobenzene. $^1$H NMR (CDCl$_3$, 500 MHz): δ (major isomer) 8.16 (s, 2H), 1.37 (br s, 24H), (minor isomer) 8.15 (s, 2H), 1.37 (br s, 24H); $^{13}$C NMR {$^1$H} (CDCl$_3$, 75 MHz): δ (major isomer) 140.1 (C4, 2C), 135.4 (br, C3, 2C), 120.1 (C2, 2C), 117.4 (nitrile, C1, 2C), 85.4, 24.7; $^{11}$B NMR (CDCl$_3$, 96 MHz): δ 30.16; FT-IR (neat): 2984, 2230, 1497, 1416, 1391, 1347, 1287, 1267, 1169, 1140, 1100, 962, 927, 855, 814, 711, 598 cm$^{-1}$; LRMS (% rel. int.): m/e (major isomer) 380 M$^+$ (35), 365 (69), 339 (100), 322 (69), 281 (46); Anal. Calcd for $C_{20}H_{26}B_2N_2O_4$: C, 63.21; H, 6.90; N, 7.37. Found: C, 63.39, H, 7.19; N, 7.02.

EXAMPLE 19

Diborylation of 4-(trifluoromethyl)-benzonitrile

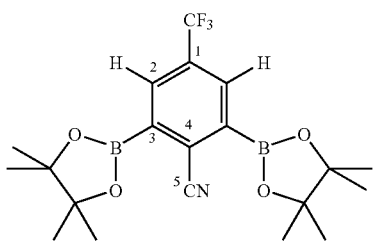

General procedure C was applied to 4-(trifluoromethyl)-benzonitrile (171.2 mg, 1 mmol, 1 equivalent) and HBPin (580 μL, 512 mg, 4 mmol, 4 equivalent) with a reaction time of 36 h. Solvent was removed under reduced pressure, and the crude mixture was eluted with CH$_2$Cl$_2$ through a plug of silica gel to afford single diborylated isomer (350 mg, 83%) as a white solid. $^{13}$C NMR spectroscopy were used to assign the single isomer as 4-(trifluoromethyl)-2,6-bis-(4,4,5,5-tetramethyl-1,3,2-dioxaboryl)-benzonitrile. $^1$H NMR (CDCl$_3$, 300 MHz): δ 8.12 (s, 2H), 1.37 (br s, 12H); $^{13}$C NMR {$^1$H} (CDCl$_3$, 75 MHz): δ 133.9 (q, $^3J_{C-F}$=3 Hz, C2), 132 (q, $^2J_{C-F}$=32.2 Hz, C1), 125 (nitrile, C5), 123.3 (q, $^1J_{C-F}$=273 Hz, CF$_3$), 117.1 (C4), 85.2, 24.7; $^{11}$B NMR (CDCl$_3$, 96 MHz): δ 30.14; $^{19}$F NMR (CDCl$_3$, 282 MHz): δ −63.3; FT-IR (neat): 2982, 2936, 2234, 1582, 1469, 1431, 1383, 1373, 1334, 1319, 1290, 1269, 1245, 1140, 1080, 966, 883, 846, 690 cm$^{-1}$; LRMS (% rel. int.): m/e 423 M$^+$ (45), 408 (100), 382 (36), 324 (45), 282 (62); Anal. Calcd for $C_{20}H_{26}B_2F_3NO_4$: C, 56.78; H, 6.19; N, 3.31. Found: C, 56.81; H, 5.92; N, 3.29; HRMS Calcd for $C_{20}H_{26}B_2F_3NO_4$: 423.2000. Found: 423.1999.

EXAMPLE 20

Borylation of 1,5-dimethyl-2-pyrrolecarbonitrile

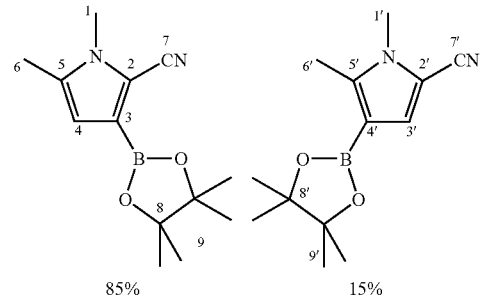

85%    15%

General procedure B was applied to 1,5-dimethyl-2-pyrrolecarbonitrile (240.3 mg, 2 mmol, 1 equivalent) and HBPin (435 μL, 384 mg, 3 mmol, 1.5 equivalents) with a reaction time of 16 h. The ratio of the two isomers in the crude reaction mixture by GC was 85:15. Solvent was removed under reduced pressure, and the crude mixture was eluted with CH$_2$Cl$_2$ through a plug of silica gel to afford a mixture of two isomeric borylated products (394 mg, 80%) as a white solid. The ratio of the two isomers in the isolated product by GC was 82:18. The NOESY1D and gHMBC spectra (FIG. 9) were used to assign the major isomer as 1,5-dimethyl-3-(4,4,5,5-tetramethyl-1,3,2-dioxaboryl)-2-pyrrolecarbonitrile. $^1$H NMR (CDCl$_3$, 300 MHz): δ (major isomer) 6.21 (d, $^4$J=0.7 Hz, 1H, pyrrol ring H), 3.63 (s, 3H, N—CH$_3$), 2.21 (d, $^4$J=0.7 Hz, 3H, CH$_3$ on pyrrol ring), 1.30 (br s, 12H), (minor isomer) 7.03 (s, 1H, pyrrol ring H), 3.6 (s, 3H, N—CH$_3$), 2.41 (s, 3H, CH$_3$ on pyrrol ring), 1.27 (s, 12H); $^{13}$C NMR {$^1$H} (CDCl$_3$, 125 MHz): δ (major isomer) 135.4 (C5), 114 (C4), 113.8 (nitrile C7), 109.6 (C2), 83.0 (C8), 32.0 (C1), 24.3 (C9), 11.8 (C6), (minor isomer) 143.9 (C5'), 125.2 (C3'), 113.7 (nitrile C7'), 103.8 (C2'), 82.6 (C8'), 31.8 (C1'), 24.4 (C9'), 11.9 (C6'); $^{11}$B NMR (CDCl$_3$, 96 MHz): δ 32.75; FT-IR (neat): 2980. 2934, 2735, 1561, 1501, 1441, 1408, 1390, 1379, 1371, 1313, 1262, 1187, 1167, 1144, 1111, 1017, 860, 835, 708 cm$^{-1}$; LRMS (% rel. int.): m/e (major isomer) 246 M$^+$ (100), 231 (19), 203 (12), 189 (16), 160 (13), 146 (20), (minor isomer) 246 M$^+$ (100), 231 (20), 189 (51), 160 (21), 146 (43); Anal. Calcd for C$_{13}$H$_{19}$BN$_2$O$_2$: C, 63.44; H, 7.78; N, 11.38. Found: C, 63.34; H, 7.78; N, 11.34.

EXAMPLE 21

Borylation of 5-methyl-2-furonitrile

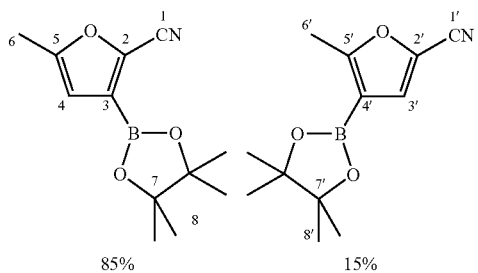

85%  15%

General procedure B was applied to 5-methyl-2-furonitrile (210 uL, 214.2 mg, 2 mmol, 1 equivalent) and HBPin (435 μL, 384 mg, 3 mmol, 1.5 equivalents) with a reaction time of 0.5 h. The ratio of the two isomers in the crude reaction mixture by GC was 85:15. Solvent was removed under reduced pressure, and the crude mixture was eluted with CH$_2$Cl$_2$ through a plug of silica gel to afford a mixture of two isomeric borylated products (456 mg, 97%) as a white solid. The ratio of the two isomers in the isolated product by GC was 90:10. The NOESY1D and gHMBC spectra (FIG. 10) were used to assign the major isomer as 5-methyl-3-(4,4,5,5-tetramethyl-1,3,2-dioxaboryl)-2-furonitrile. $^1$H NMR (CDCl$_3$, 300 MHz): δ (major isomer) 6.23 (d, $^4$J=1.0 Hz, 1H, furan ring H), 2.29 (d, $^4$J=1.0 Hz, 3H, CH$_3$ on furan ring), 1.27 (br s, 12H), (minor isomer) 7.12 (s, 1H, furan ring H), 2.46 (s, 3H, CH$_3$ on furan ring), 1.25 (s, 12H); $^{13}$C NMR {$^1$H} (CDCl$_3$, 75 MHz): δ (major isomer) 157.6 (C5), 130.4 (C2), 111.9 (nitrile C1), 111.5 (C4), 84.3 (C7), 24.6 (C8), 13.4 (C6), (minor isomer) 167 (C5'), 127.4 (C3'), 124.1 (C2'), 111.7 (nitrile C1'), 83.8 (C7'), 24.7 (C8'), 14.2 (C6'); $^{11}$B NMR (CDCl$_3$, 96 MHz): δ 28.9; FT-IR (neat): 2982, 2934, 1595, 1543, 1446, 1428, 1408, 1392, 1381, 1373, 1335, 1302, 1228, 1169, 1143, 1043, 963, 855, 804, 712 cm$^{-1}$; LRMS (% rel. int.): m/e (major isomer) 233 M$^+$ (89), 218 (42), 203 (20), 190 (64), 175 (59), 149 (100), 134 (47), (minor isomer) 233 M$^+$ (100), 218 (81), 191 (54), 175 (62), 149 (53), 133 (63); Anal. Calcd for C$_{12}$H$_{16}$BNO$_3$: C, 61.84; H, 6.92; N, 6.01. Found: C, 62.25; H, 7.0; N, 5.80.

EXAMPLE 22

Borylation of 5-bromo-2-cyanopyridine

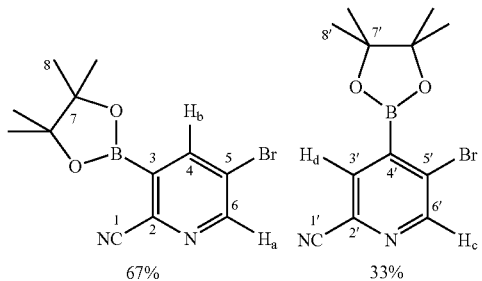

67%  33%

General procedure B was applied to 5-bromo-2-cyanopyridine (183 mg, 1 mmol, 1 equivalent) and HBPin (290 μL, 256 mg, 2 mmol, 2 equivalent) with a reaction time of 18 h. The ratio of the two isomers in the crude reaction mixture by $^1$H NMR spectroscopy was 67:33. Kugelrohr distillation furnished a mixture of the two isomeric borylated products (253.5 mg, 81%) as a white solid. The ratio of the two isomers in the isolated product by $^1$H NMR spectroscopy was 64:36. $^1$H NMR and gHMBC spectroscopy were used to assign the major isomer as 5-bromo-3-(4,4,5,5-tetramethyl-1,3,2-dioxaboryl)-2-cyanopyridine. $^1$H NMR (CDCl$_3$, 300 MHz): δ (major isomer) 8.76 (d, J=2.4 Hz, 1H, H$_a$), 8.28 (d, J=2.4 Hz, 1H, H$_b$), 1.37 (br s, 12H), (minor isomer) 8.76 (s, 1H, H$_c$), 7.85 (s, 1H, H$_d$), 1.36 (s, 12H); $^{13}$C NMR {$^1$H} (CDCl$_3$, 75 MHz): δ (major isomer) 153.6 (C6), 145.8 (C4), 136.1 (C2), 124.4 (C5), 116.6 (nitrile C1), 85.7 (C7), 24.8 (C8), (minor isomer) 153.1 (C6'), 134.5 (C3'), 131.4 (C2'), 130.1 (C5'), 116.7 (nitrile C1'), 85.6 (C7'), 24.8 (C8'); $^{11}$B NMR (CDCl$_3$, 96 MHz): δ 29.5; FT-IR (neat): 3048, 2979, 2244, 1566, 1539, 1416, 1383, 1342, 1318, 1269, 1142, 1069, 1026, 964, 872, 847, 771 cm$^{-1}$; LRMS (% rel. int.): m/e (major isomer) 308 M$^+$ (41), 310 (M$^{2+}$ 37), 293 (95), 267 (96), 250 (65), 229 (34), 209 (42), (minor isomer) 308 M$^+$ (7), 293 (33), 267 (17), 229 (100), 187 (91); Anal. Calcd for C$_{12}$H$_{14}$BBrN$_2$O$_2$: C, 46.65; H, 4.57; N, 9.07. Found: C, 46.52; H, 4.48; N, 8.761.

EXAMPLE 23

Borylation of 2-Cyano-5-Bromopyridine

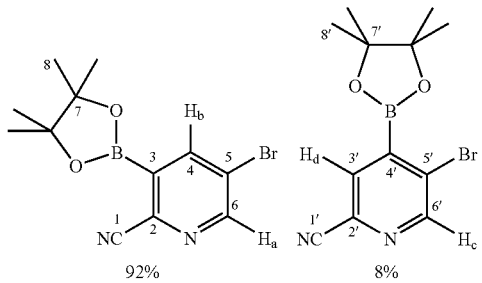

92%  8%

In a glove box, a 20 mL scintillation vial equipped with a magnetic stirring bar, was charged with 2,2'-bis[(4S)-4-benzyl-2-oxazoline] (9.6 mg, 0.03 mmol, 3 mol %). Ether (1 mL) was added to the scintillation vial in order to dissolve the ligand. [Ir(OMe)(COD)]$_2$ (10 mg, 0.015 mmol, 3 mol % Ir) was weighed in a test tube. HBPin (218 μL, 192 mg, 1.50 mmol, 1.50 equiv) and ether (1 mL) were added to the [Ir(OMe)(COD)]$_2$ containing test tube. The resulting solution was transferred to the 20 mL scintillation vial. Additional ether (1 mL) was used to wash the test tube and the washings were transferred to the scintillation vial. 2-cyano-5-bromopyridine (183 mg, 1 mmol, 1 equiv) was then added to the scintillation vial and the reaction mixture was stirred at room temperature for 12 h. The ratio of two borylated products at the end of reaction was 92:8 by GC-FID. Kugelrohr distillation gave mixture of monoborylated products as a white solid (263 mg, 85% yield). $^1$H NMR (CDCl$_3$, 300 MHz): δ (major isomer) 8.76 (d, J=2.4 Hz, 1H, H$_a$), 8.28 (d, J=2.4 Hz, 1H, H$_b$), 1.37 (br s, 12 H, CH$_3$ of BPin), (minor isomer) 8.76 (s, 1H, H$_c$), 7.85 (s, 1H, H$_d$), 1.36 (s, 12H, CH$_3$ of BPin); $^{13}$C NMR {$^1$H} (CDCl$_3$, 75 MHz): δ (major isomer) 153.6 (CH, C6), 145.8 (CH, C4), 136.1 (C, C2), 124.4 (C, C5), 116.6 (C, nitrile C1), 85.7 (C, C7), 24.8 (CH$_3$, C8, CH$_3$ of BPin), (minor isomer) 153.1 (CH, C6'), 134.5 (CH, C3'), 131.4 (C, C2'), 130.1 (C, C5'), 116.7 (C, nitrile C1'), 85.6 (C, C7'), 24.8 (CH$_3$, C8', CH$_3$ of BPin ); $^{11}$B NMR (CDCl$_3$, 96 MHz): δ 29.5; FT-IR (neat) $\tilde{v}_{max}$: 3048, 2979, 2244, 1566, 1539, 1416, 1383, 1342, 1318, 1269, 1142, 1069, 1026, 964, 872, 847, 771 cm$^{-1}$; GC-MS (EI) m/z (% relative intensity): (major isomer) 308 M$^+$ (41), 310 (M$^{2+}$ 37), 293 (95), 267 (96), 250 (65), 229 (34), 209 (42), (minor isomer) 308 M$^+$ (7), 293 (33), 267 (17), 229 (100), 187 (91); Anal. Calcd for C$_{12}$H$_{14}$BBrN$_2$O$_2$: C, 46.65; H, 4.57; N, 9.07. Found: C, 46.52; H, 4.48; N, 8.761.

EXAMPLE 24

The procedure in Example 23, replacing 2,2'-bis[(4S)-4-benzyl-2-oxazoline] with 2,2'-bis (2-oxazoline) as the ligand, was applied to 2-cyano-5-bromopyridine (183 mg, 1 mmol, 1 equiv) for 6 h. The ratio of two borylated products at the end of reaction was 78:22 by GC-FID. Kugelrohr distillation gave a mixture of monoborylated products as a white solid (242 mg, 78% yield).

EXAMPLE 25

Borylation of 2-Bromo-5-Cyanothiophene

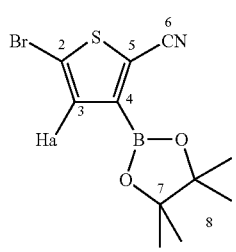

The general procedure in Example 23 was applied to 2-bromo-5-cyanothiophene (111 μL, 188 mg, 1 mmol, 1 equiv) and HBPin (290 μL, 256 mg, 2.00 mmol, 2.00 equiv) with 6% [Ir] catalyst loading for 16 h. Volatile materials were removed on a rotary evaporator. The crude material was dissolved in CH$_2$Cl$_2$ and passed through a short plug of silica to afford the borylated product as a white solid (284 mg, 90% yield, mp 98-100° C.) with >98% isomeric purity by GC-FID. $^1$H NMR (CDCl$_3$, 500 MHz): δ 7.30 (s, 1H, H$_a$), 1.30 (br s, 12H, CH$_3$ of BPin); $^{13}$C NMR {$^1$H} (CDCl$_3$, 125 MHz): δ 136.0 (CH), 119.1 (C), 118.8 (C), 113.1 (C), 84.9 (C), 24.7 (CH$_3$, CH$_3$ of BPin); $^{11}$B NMR (CDCl$_3$, 96 MHz): δ 28.0; GC-MS (EI) m/z (% relative intensity): M$^+$ 315 (100), 313 (97), 314 (59), 300 (32), 298 (30), 272 (85), 257 (47), 255 (48), 229 (22), 192 (76); Anal. Calcd for C$_{11}$H$_{13}$BBrNO$_2$S: C, 42.07; H, 4.17; N, 4.46. Found: C, 42.32; H, 4.11; N, 4.50. It was not possible to borylated this substrate using d$^t$bpy ligand.

EXAMPLE 26

Borylation of 2-Cyano-5-Methylfuran

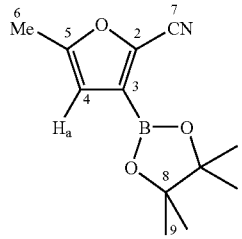

In a glove box, a 20 mL scintillation vial equipped with a magnetic stirring bar, was charged with 2,2'-bis[(4S)-4-benzyl-2-oxazoline] (9.6 mg, 0.03 mmol, 3 mol %). Ether (1 mL) was added to the scintillation vial in order to dissolve the ligand. [Ir(OMe)(COD)]$_2$ (10 mg, 0.015 mmol, 3 mol % Ir) was weighed in a test tube. HBPin (218 μL, 192 mg, 1.50 mmol, 1.50 equiv) and ether (1 mL) were added to the [Ir(OMe)(COD)]$_2$ containing test tube. The resulting solution was transferred to the 20 mL scintillation vial. Additional ether (1 mL) was used to wash the test tube and the washings were transferred to the scintillation vial. 2-cyano-5-methylfuran (105 μL, 107 mg, 1 mmol, 1 equiv) was added and the mixture was stirred at room temperature for 3 h. Volatile materials were removed on a rotary evaporator. The crude material was dissolved in CH$_2$Cl$_2$ and passed through a short plug of silica to afford the borylated product as a white solid (225 mg, 96% yield) with >99% isomeric purity by $^1$H NMR. $^1$H NMR (CDCl$_3$, 300 MHz): δ 6.24 (d, J=1.0 Hz, 1H, H$_a$), 2.31 (d, J=1.0 Hz, 3 H, CH$_3$), 1.30 (br s, 12H, CH$_3$ of BPin); $^{13}$C NMR {$^1$H} (CDCl$_3$, 75 MHz): δ 157.7 (C), 130.5 (C), 112.0 (C), 111.5 (CH), 84.4 (C), 24.7 (CH$_3$, CH$_3$ of BPin), 13.5 (CH$_3$); $^{11}$B NMR (CDCl$_3$, 96 MHz): δ 28.9; GC-MS (EI) m/z (% relative intensity): M$^{+1}$ 234 (100), 233 (98), 218 (23), 203 (16), 190 (41), 175 (23).

EXAMPLE 27

Diborylation of 2-Cyanothiophene

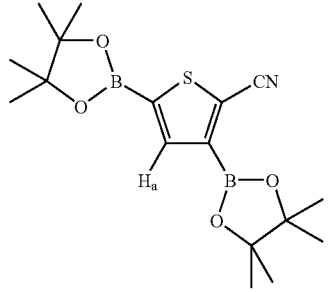

In a glove box, a 20 mL vial, equipped with a magnetic stirring bar, was charged with {Ir(OMe)(COD)}$_2$ (20 mg, 0.03 mmol, 6 mol % Ir), d$^t$bpy (16.1 mg, 0.06 mmol, 6 mol %), and excess HBPin (4 equivalent of boron). These reagents were dissolved in 3 mL of THF, 2-cyanothiophene (94 µL, 109 mg, 1 mmol, 1 equiv) was added, and the mixture was stirred at room temperature for 1 h. Volatile materials were removed on a rotary evaporator. The crude material was dissolved in CH$_2$Cl$_2$ and passed through a short plug of silica to afford the borylated product as a white solid (317 mg, 88% yield, mp 132-133° C.). $^1$H NMR (CDCl$_3$, 500 MHz): δ 7.87 (s, 1H, H$_a$), 1.33 (br s, 12 H, CH$_3$ of BPin), 1.31 (br s, 12H, CH$_3$ of BPin); $^{13}$C NMR {$^1$H} (CDCl$_3$, 125 MHz): δ 143.1 (CH), 123.2 (C), 114.3 (C), 84.8 (C), 84.6 (C), 24.8 (CH$_3$, CH$_3$ of BPin), 24.7 (CH$_3$, CH$_3$ of BPin); $^{11}$B NMR (CDCl$_3$, 96 MHz); δ 28.6; FT-IR (neat) $\tilde{v}_{max}$: 2980, 2934, 2220, 1532, 1458, 1373, 1319, 1138, 966, 848, 667 cm$^{-1}$; GC-MS (EI) m/z (% relative intensity): M$^{+1}$ 361 (73), 360 (39), 346 (53), 320 (100), 303 (31); Anal. Calcd for C$_{17}$H$_{25}$B$_2$NO$_4$S: C, 56.55; H, 6.98; N, 3.88. Found: C, 56.45; H, 7.16; N, 3.84.

EXAMPLE 28

Diborylation of 3-Cyanothiophene

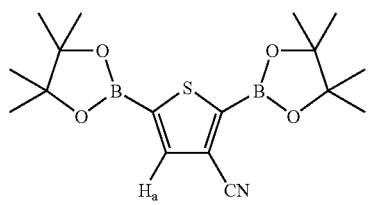

In a glove box, a 20 mL vial, equipped with a magnetic stirring bar, was charged with {Ir(OMe)(COD)}$_2$ (20 mg, 0.03 mmol, 6 mol % Ir), d$^t$bpy (16.1 mg, 0.06 mmol, 6 mol %), and excess HBPin (4 equivalent of boron). These reagents were dissolved in 3 mL of THF, 3-cyanothiophene (91 µL, 109 mg, 1 mmol, 1 equiv) was added, and the mixture was stirred at room temperature for 30 min. Volatile materials were removed on a rotary evaporator. The crude material was dissolved in CH$_2$Cl$_2$ and passed through a short plug of silica to afford the borylated product as a white solid (306 mg, 85% yield). $^1$H NMR (CDCl$_3$, 500 MHz): δ 7.80 (s, 1H, H$_a$), 1.34 (br s, 12H, CH$_3$ of BPin), 1.31 (br s, 12H, CH$_3$ of BPin); $^{11}$B NMR (CDCl$_3$, 96 MHz); δ 28.8.

EXAMPLE 29

Mono borylation of 3-Cyanothiophene

In a glove box, a 20 mL scintillation vial equipped with a magnetic stirring bar, was charged with 2,2'-bis[(4S)-4-benzyl-2-oxazoline]0 (9.6 mg, 0.03 mmol, 3 mol %). Ether (1 mL) was added to the scintillation vial in order to dissolve the ligand. [(Ir(OMe)(COD)]$_2$ (10 mg, 0.015 mmol, 3 mol % Ir) was weighed in a test tube. HBPin (145 µL, 128 mg, 1 mmol, 1 equiv) and ether (1 mL) were added to the [Ir(OMe)(COD)]$_2$ containing test tube. The resulting solution was transferred to the 20 mL scintillation vial. Additional ether (1 mL) was used to wash the test tube and the washings were transferred to the scintillation vial. 3-cyanothiophene (182 µL, 218 mg, 2.00 mmol, 2.00 equiv) was then added to the scintillation vial and the reaction mixture was stirred at room temperature for 1 h. Volatile materials were removed on a rotary evaporator. The crude material was dissolved in CH$_2$Cl$_2$ and passed through a short plug of silica to afford a mixture of borylated isomers (37% 2-(4,4,5,5-tetramethyl-1, 3,2-dioxaboryl)-4-cyanothiophene and 63% 2-(4,4,5,5-tetramethyl-1,3,2-dioxaboryl)-3-cyanothiophene). (Note: 2-(4, 4,5,5-tetramethyl-1,3,2-dioxaboryl)-3-cyanothiophene has been prepared by other methods (Christophersen, C. et al., J. Org. Chem. 2003, 68, 9513-9516 and Blackaby, W. P. et al. PCT Int. Appl. WO 2002076983), but never isolated.

2-(4,4,5,5-tetramethyl-1,3,2-dioxaboryl)-4-cyanothiphene; $^1$H NMR (CDCl$_3$, 500 MHz): δ 8.13 (d, J=1.2 Hz, 1H), 7.74 (d, J=1.2 Hz, 1H), 1.31 (br s, 12H, CH$_3$ of BPin).

2-(4,4,5,5-tetramethyl-1,3,2-dioxaboryl)-3-cyanothiphene; $^1$H NMR (CDCl$_3$, 500 MHz): δ 7.62 (d, J=4.9 Hz, 1H), 7.37 (d, J=4.9 Hz, 1H), 1.34 (br s, 12H, CH$_3$ of BPin).

EXAMPLE 30

The procedure in Example 29 was followed using 2,2'-bis (2-oxazoline) in place 2,2'-bis[(4S)-4-benzyl-2-oxazoline]. The crude material was dissolved in CH$_2$Cl$_2$ and passed through a short plug of silica to afford a mixture of borylated isomers (14% 2-(4,4,5,5-tetramethyl-1,3,2-dioxaboryl)-4-cyanothiphene and 86% 2-(4,4,5,5-tetramethyl-1,3,2-dioxaboryl)-3-cyanothiphene).

The effects of ligand on the regioselectivity for the mono borylation of 3-cyanothiophene is shown below.

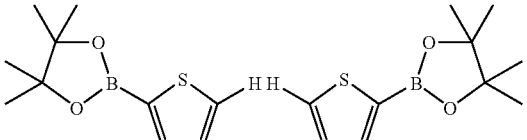

EXAMPLE 31

Mono Borylation of 4-Chlorobenzonitrile

In a glove box, a 20 mL vial, equipped with a magnetic stirring bar, was charged with {Ir(OMe)(COD)}$_2$ (5.0 mg, 0.0075 mmol, 3 mol % Ir), 2,2'-bis[(4S)-4-benzyl-2-oxazoline] (4.8 mg, 0.015 mmol, 3 mol %). 4,4'-di-t-butyl-2,2'-bipyridine (d$^t$bpy) (4.0 mg, 0.015 mmol, 3 mol %), and pinacolborane (HBPin) (73 μL, 64 mg, 0.5 mmol, 1 equivalent). These reagents were dissolved in 2 mL of THF, 4-chlorobenzonitrile (275 mg, 2.00 mmol, 4.00 equiv) was added, and the mixture was stirred at room temperature for 48 h. 4-chloro-2-(4,4,5,5-tetramethyl-1,3,2-dioxaboryl)benzonitrile (93%) and 4-chloro-3-(4,4,5,5-tetramethyl-1,3,2-dioxaboryl)benzonitrile (7%) were formed as a mixture of isomers.

EXAMPLE 32

Borylation of 1,3-dicyanobenzene

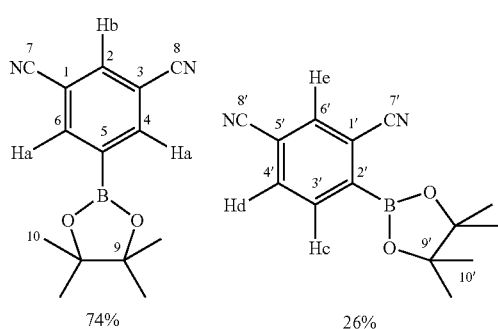

General procedure A was applied to 1,3-dicyanobenzene (256.3 mg, 2 mmol) and HBPin (73 μL, 64 mg, 0.5 mmol) with a reaction time of 12 h. The ratio of the two isomers in the crude reaction mixture by $^1$H NMR spectroscopy was 74:26. Kugelrohr distillation furnished a mixture of the two isomeric borylated products (79 mg, 62%) as a white solid. The ratio of the two isomers in the isolated product by $^1$H NMR spectroscopy was 77:23. $^1$H NMR spectroscopy was used to assign the major isomer as 5-(4,4,5,5-tetramethyl-1,3,2-dioxaboryl)-1,3-dicyanobenzene. $^1$H NMR (CDCl$_3$, 300 MHz): δ (major isomer) 8.24 (d, J=1.7 Hz, 2H, H$_a$), 7.96 (t, J=1.7 Hz, 1H, H$_b$), 1.33 (br s, 12H), (minor isomer) 7.99 (d, J=7.8 Hz, 1H, H$_c$), 7.92 (d, J=1.4 Hz, 1H, H$_e$), 7.80 (dd, J=7.8, 1.4 Hz, 1H, H$_d$), 1.36 (br s, 12H); $^{13}$C NMR {$^1$H}(CDCl$_3$, 125 MHz):δ (major, meta isomer) 141.8 (C4, C6), 137.1 (C2), 116.7 (nitrile C7, C8), 113.5 (C1, C3), 85.2 (C9), 24.8 (C10), (minor, ortho isomer) 136.6, 136.1, 134.4, (C3', C4', C6') 118.6, 116.8, 116.7, 115.3, (C1', C5', C7', C8'), 85.5 (C9'), 24.7 (C10'). $^{11}$B NMR (CDCl$_3$, 96 MHz): δ 30.03; FT-IR (neat): 3073, 2982, 2237, 1595, 1418, 1398, 1374, 1339, 1233, 1215, 1169, 1144, 1129, 1064, 966, 897, 849, 698 cm$^{-1}$; LRMS (% rel. int.): m/e 254 M$^+$ (7), 239 (100), 211 (15), 196 (4), 168 (43), 155 (7) Anal. Calcd for C$_{14}$H$_{15}$BN$_2$O$_2$: C, 66.18; H, 5.95; N, 11.02. Found: C, 66; H, 6.02; N, 10.81.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

We claim:

1. A process for producing a cyano ring-substituted arene borane wherein the arene is selected from the group consisting of pyridine, pyrrole, furan, thiophene and benzene, the process comprising:
   reacting a ring-substituted cyano arene with an HB or a B—B organic compound, in the presence of a catalytically effective amount of a catalytic composition comprising an iridium complex and an organic ligand at least in part bonded to the iridium complex, the organic ligand being selected from the group consisting of a phosphorus organic ligand, an organic amine, an imine, and a nitrogen-substituent organic ligand comprising at least one 5- or 6-membered nitrogen heterocycle to form the cyano ring-substituted arene borane;

wherein:

(i) the iridium complex is selected from the group consisting of (Cp*)Ir(H)$_2$(Me$_3$P), (Cp*)Ir(H)(BPin)(Me$_3$P), (CP*)Ir(H)(C$_6$H$_5$)(Me$_3$P), (Ind)Ir(COD), (MesH)Ir(BPin)(B(OR)$_2$), ((R$_1$)$_3$P)$_3$Ir(B(OR$_2$)$_2$)$_3$, (R$_1$)$_2$P)$_2$Ir(BPin)$_3$, [((R$_1$)$_2$P)$_3$Ir((R$_2$O)$_2$B)$_3$]$_2$, ((R$_1$)$_3$P)$_4$Ir(BPin), ((R1)$_2$P)$_2$Ir(BPin)$_3$, (MesH)Ir(BPin)$_3$, IrCl(COD), [IrCl(COD)]$_2$, [Ir(OMe)(COD)]$_2$, and combinations thereof; and (ii) in the iridium complex, CP* is 1,2,3,4,5-methylcyclopentadienyl, BPin is pinacolborane, Me is methyl, H is hydrogen, P is phosphorus, Ind is indenyl, COD is 1,5-cyclooctadiene, MesH is mesitylene, and R, R$_1$, and R$_2$ are each selected from the group consisting of hydrogen, linear or branched alkyl containing 1 to 8 carbons, aryl, and a carbon in a cyclic structure.

2. A process for producing a di-cyano or tri-cyano ring-substituted arene borane wherein the arene is selected from the group consisting of pyridine, furan, pyrrole, thiophene and benzene, the process comprising:

reacting a di-cyano or tri-cyano ring-substituted arene with an HB or a B—B organic compound in the presence of a catalytically effective amount of a catalytic composition comprising an iridium complex and a dipyridyl organic ligand at least in part bonded to the iridium complex in a molar ratio of iridium complex to dipyridyl organic ligand between 1 to 3 and 1 to 1 to form the di-cyano or tri-cyano ring-substituted arene borane;

wherein:

(i) the iridium complex is selected from the group consisting of (Cp*)Ir(H)$_2$(Me$_3$P), (Cp*)Ir(H)(BPin)(Me$_3$P), (CP*)Ir(H)(C$_6$H$_5$)(Me$_3$P), (Ind)Ir(COD), (MesH)Ir(BPin)(B(OR)$_2$), ((R$_1$)$_3$P)$_3$Ir(B(OR$_2$)$_2$)$_3$, (R$_1$)$_2$P)$_2$Ir(BPin)$_3$, [((R$_1$)$_2$P)$_3$Ir((R$_2$O)$_2$B)$_3$]$_2$, ((R$_1$)$_3$P)$_4$Ir(BPin), ((R1)$_2$P)$_2$Ir(BPin)$_3$, (MesH)Ir(BPin)$_3$, IrCl(COD) [IrCl(COD)]$_2$, [Ir(OMe)(COD)]$_2$, and combinations thereof; and (ii) in the iridium complex, CP* is 1,2,3,4,5-methylcyclopentadienyl, BPin is pinacolborane, Me is methyl, H is hydrogen, P is phosphorus, Ind is indenyl, COD is 1,5-cyclooctadiene, MesH is mesitylene, and R, R$_1$, and R$_2$ are each selected from the group consisting of hydrogen, linear or branched alkyl containing 1 to 8 carbons, aryl, and a carbon in a cyclic structure.

3. A benzonitrile of the formula:

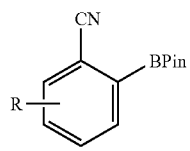

wherein R is selected from the group consisting of cyano, BPin, halo other than fluoro, alkyl, alkoxy, thioalkyl, amino alkyl, acyl, alkyl aminoacyl, trifluoro methyl, substituted aryl, organosilane, organoborane, organostannane and organophosphorus each containing 1 to 8 carbon atoms except for the halo group.

4. A process for producing a ring-substituted arene borane wherein the arene is selected from the group consisting of pyridine, furan, pyrrole, thiophene and benzene, the process comprising:

reacting a ring-substituted arene having one to five substituents of which one or more is a cyano group, with HBPin or B$_2$Pin$_2$, in the presence of a catalytically effective amount of a catalytic composition comprising an iridium complex and a nitrogen-substituent organic ligand at least in part bonded to the iridium complex to form a ring-substituted arene borane containing two to six substituents at least one of which is a cyano group;

wherein:

(i) the iridium complex is selected from the group consisting of (Cp*)Ir(H)$_2$(Me$_3$P), (Cp*)Ir(H)(BPin)(Me$_3$P), (CP*)Ir(H)(C$_6$H$_5$)(Me$_3$P), (Ind)Ir(COD), (MesH)Ir(BPin)(B(OR)$_2$), ((R$_1$)$_3$P)$_3$Ir(B(OR$_2$)$_2$)$_3$, (R$_1$)$_2$P)$_2$Ir(BPin)$_3$, [((R$_1$)$_2$P)$_3$Ir((R$_2$O)$_2$B)$_3$]$_2$, ((R$_1$)$_3$P)$_4$Ir(BPin), ((R1)$_2$P)$_2$Ir(BPin)$_3$, (MesH)Ir(BPin)$_3$, IrCl(COD) [IrCl(COD)]$_2$, [Ir(OMe)(COD)]$_2$, and combinations thereof; and (ii) in the iridium complex, CP* is 1,2,3,4,5-methylcyclopentadienyl, BPin is pinacolborane, Me is methyl, H is hydrogen, P is phosphorus, Ind is indenyl, COD is 1,5-cyclooctadiene, MesH is mesitylene, and R, R$_1$, and R$_2$ are each selected from the group consisting of hydrogen, linear or branched alkyl containing 1 to 8 carbons, aryl, and a carbon in a cyclic structure;

(iii) the nitrogen-substituent organic ligand comprises at least one 5- or 6-membered nitrogen heterocycle; and (iv) the catalytic composition has a molar ratio of the iridium complex to the organic ligand between 1 to 3 and 1 to 1.

5. The process of claim 4 wherein the borane moiety is ortho to a cyano group in the ring-substituted arene borane produced.

6. The process of claim 1 or 4 wherein the nitrogen-substituent organic ligand is selected from the group consisting of:

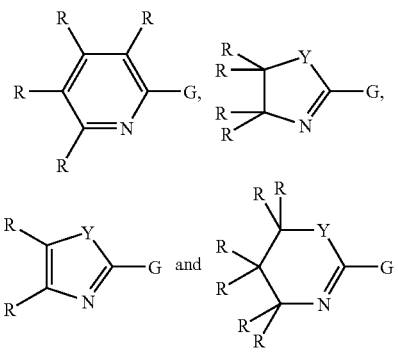

wherein R are each selected from the group consisting of hydrogen, linear alkyl containing 1 to 8 carbon atoms, branched alkyl containing 1 to 8 carbons, and a carbon in a cyclic structure, Y is a carbon, oxygen, nitrogen, or sulfur containing moiety, and G is a heteroatom containing group, multiple atom chain, or multiple atom ring.

7. The process of claim 1 or 4 wherein the nitrogen-substituent organic ligand is selected from the group consisting of:

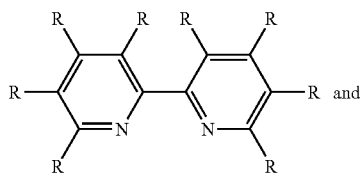

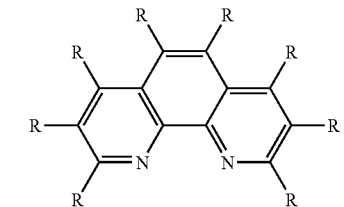

wherein R are each selected from the group consisting of hydrogen, linear alkyl containing 1 to 8 carbon atoms, branched alkyl containing 1 to 8 carbons, and a carbon in a cyclic structure.

8. The process of claim 1 or 4 wherein the nitrogen-substituent organic ligand is selected from the group consisting of:

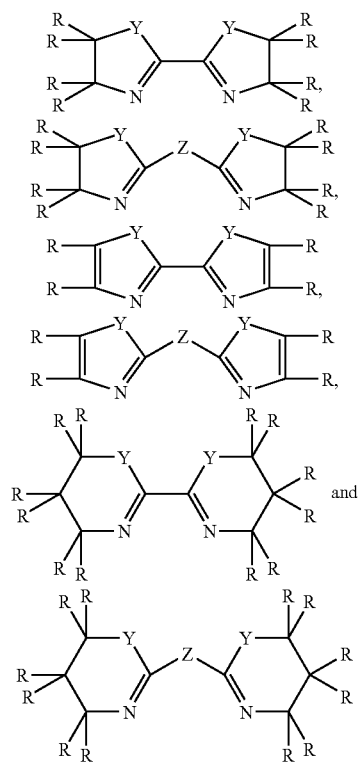

wherein R are each selected from the group consisting of hydrogen, linear alkyl containing 1 to 8 carbon atoms, branched alkyl containing 1 to 8 carbons, and a carbon in a cyclic structure, Y is a carbon, oxygen, nitrogen, or sulfur containing moiety, and Z is a carbon, oxygen, nitrogen, sulfur, or boron containing moiety or a multiple atom chain containing a carbon, oxygen, nitrogen, sulfur, or boron containing moiety.

9. The process of claim 1 or 2 wherein the HB or B—B organic compound is HBPin or $B_2Pin_2$.

10. The process of claim 1 or 4 wherein the iridium complex comprises [Ir(OMe)(COD)] and the nitrogen-substituent organic ligand comprises 4,4'-di-t-butyl-2,2'-bipyridine (dt-bpy).

11. A benzonitrile of the formula:

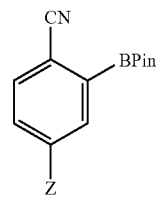

wherein BPin is

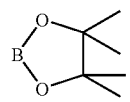

and Z is selected from the group consisting of —CH₃, —OMe, —SMe, —NMe₂, —CO₂Me, —NHAc, and —CF₃ moieties.

12. A 2-cyano-3-borylated-pyridine of the formula:

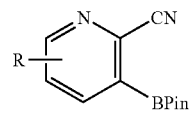

wherein R is selected from the group consisting of cyano, BPin, halo other than fluoro, alkyl, alkoxy, thioalkyl, amino, alkyl acyl, alkyl aminoacyl, trifluoro methyl, substituted aryl, organosilane, organoborane, organostannane and organophosphorus containing 1 to 8 carbon atoms except for the halo group.

13. A 5-cyano-4-borylated-thiophene of the formula:

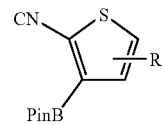

wherein R is selected from the group consisting of cyano, BPin, halo other than fluoro, alkyl, alkoxy, thioalkyl, amino, alkyl acyl, alkyl aminoacyl, trifluoro methyl, substituted aryl, organosilane, organoborane, organostannane and organophosphorus containing 1 to 8 carbon atoms except for the halo group.

14. A 2-cyano-3-borylated-furan of the formula:

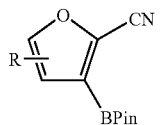

wherein R is selected from the group consisting of cyano, BPin, halo other than fluoro, alkyl, alkoxy, thioalkyl, amino, alkyl acyl, alkyl aminoacyl, trifluoro methyl, substituted aryl, organosilane, organoborane, organostannane and organophosphorus containing 1 to 8 carbon atoms except for the halo group.

15. A 5-cyano-2,4-di BPin thiophene.

16. A 4-cyano-2,5-di BPin thiophene.

17. The process of claim 1, 2, or 4 wherein the iridium complex is selected from [Ir(OMe)(COD)]$_2$, [IrCl(COD)]$_2$, (Ind)Ir(COD), and combinations thereof.

* * * * *

UNITED STATES PATENT AND TRADEMARK OFFICE
CERTIFICATE OF CORRECTION

PATENT NO. : 7,514,563 B2  Page 1 of 1
APPLICATION NO. : 11/449280
DATED : April 7, 2009
INVENTOR(S) : Milton R. Smith, III, Robert E. Maleczka and Ghayoor A. Chotana It is certified that error appears in the above-identified patent and that said Letters Patent is hereby corrected as shown below:

Column 9, line 64, "Chem. 1999, 7707" should be --Chem. 1999, 64, 7707--.

Column 15, line 23, "1:5 mol %" should be --1.5 mol %--.

Column 20, line 9, "$^1J_{C-F}$-261.3" should be --$^1J_{C-F}$=261.3--.

Column 29, lines 30-40, " " should be -- --.

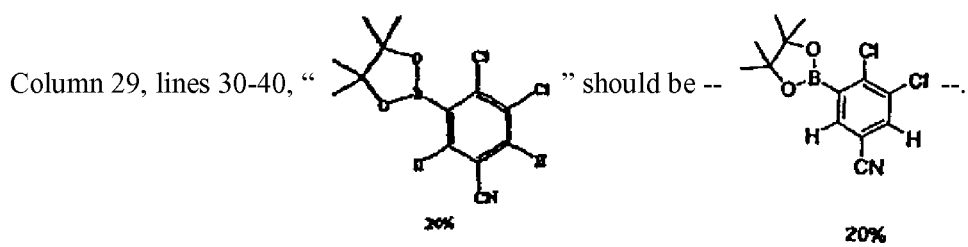

Column 36, line 30, "$^1$II NMR and gIIMBC" should be --$^1$H NMR and gHMBC--.

Column 40, line 21, "oxazoline]0(9.6 mg" should be --oxazoline] (9.6 mg--.

Signed and Sealed this

Twenty-fifth Day of August, 2009

David J. Kappos
*Director of the United States Patent and Trademark Office*

UNITED STATES PATENT AND TRADEMARK OFFICE
CERTIFICATE OF CORRECTION

PATENT NO. : 7,514,563 B2  
APPLICATION NO. : 11/449280  
DATED : April 7, 2009  
INVENTOR(S) : Milton R. Smith, III et al.

Page 1 of 1

It is certified that error appears in the above-identified patent and that said Letters Patent is hereby corrected as shown below:

In the Specification

In column 1, lines 14-17, please delete:

"This invention was supported in part by National Institutes of Health, National Institute of General Medical Sciences Grant No. R01 GM63188-01. The U.S. government has certain rights in this invention."

and insert:

-- This invention was made with government support under GM063188 awarded by the National Institutes of Health. The government has certain rights in the invention. --

Signed and Sealed this  
Twelfth Day of August, 2014

Michelle K. Lee  
*Deputy Director of the United States Patent and Trademark Office*